United States Patent
Freyne et al.

(10) Patent No.: US 6,803,364 B1
(45) Date of Patent: Oct. 12, 2004

(54) IL-5 INHIBITING 6-AZAURACIL DERIVATIVES

(75) Inventors: Eddy Jean Edgard Freyne, Rumst (BE); Frederik Dirk Deroose, Sint Amandsberg (BE); Jean Fernand Armand Lacrampe, Le Mesnil-Esnard (FR); Werner Constant Johan Embrechts, Beerse (BE); Jerome Michel Claude Fortin, Lery (FR)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 09/868,384

(22) PCT Filed: Dec. 16, 1999

(86) PCT No.: PCT/EP99/10169

§ 371 (c)(1),
(2), (4) Date: Aug. 29, 2001

(87) PCT Pub. No.: WO00/37451

PCT Pub. Date: Jun. 29, 2000

(30) Foreign Application Priority Data

Dec. 18, 1998 (EP) .............................................. 98204336

(51) Int. Cl.$^7$ ........................ C07D 253/06; A61K 31/53
(52) U.S. Cl. ........................................ 514/242; 544/182
(58) Field of Search ........................... 514/242; 544/182

(56) References Cited

U.S. PATENT DOCUMENTS

| | | |
|---|---|---|
| 3,883,528 A | 5/1975 | Mylan |
| 3,912,723 A | 10/1975 | Miller |
| 4,631,278 A | 12/1986 | Boeckx et al. |
| 4,767,760 A | 8/1988 | Boeckx et al. |
| 4,931,444 A | 6/1990 | Van Wauwe et al. |
| 5,256,631 A | 10/1993 | Lindner et al. |

FOREIGN PATENT DOCUMENTS

| | | |
|---|---|---|
| DE | 2149645 | 9/1972 |
| EP | 0 232 932 A | 8/1987 |
| EP | 170 316 B1 | 5/1990 |
| EP | 476 439 A1 | 3/1992 |
| EP | 737 672 A2 | 10/1996 |
| EP | 0 831 088 | 3/1998 |
| EP | 648 760 B1 | 1/1999 |
| WO | WO 94/14742 A1 | 7/1994 |
| WO | WO 94/20446 A1 | 9/1994 |
| WO | WO 96/31485 A1 | 10/1996 |
| WO | WO 99 02504 A | 1/1999 |
| WO | WO 99 02505 A | 1/1999 |

OTHER PUBLICATIONS

Carroll et al., "Anticoccidial Derivatives of 6-Azauracil 5. Potentiation by Benzophenone Side Chains," J. Med. Chem. 1983, pp. 96–100, vol. 26.

Baggiolini et al., "CC Chemokines in Allergic Inflammation." *Immunology Today*, 1994, pp. 127–133, vol. 15, No. 3.

Carr et al., "Expression On Porcine γ δ lymphocytes Of A Phylogenetically Conserved Surface Antigen Previously Restricted In Expression γ δT Lymphocytes," *Immunology*, 1994, pp. 36–40, vol. 81.

Minnicozzi, et al., "The inhibition of interleuken 5 in allergic diseases," *Exp. Opin. Ther. Patents*, 1999, pp. 147–156, vol. 2, No. 9.

Mishra et al., "IL-5 Promotes Eosinophil Trafficking to the Esophagus." *The Journal of Immunology*, 2002, pp. 2464–2469, vol. 168.

*Primary Examiner*—Bruck Kifle
(74) *Attorney, Agent, or Firm*—Gabriel Lopez; Alana G. Kriegeman

(57) ABSTRACT

The present invention is concerned with the compounds of formula (I), a N-oxide, a pharmaceutically acceptable addition salt, a quaternary amine or a stereochemically isomeric form thereof, wherein p is 0 to 4; q is 0 to 5; X is O, S, NR$^3$ or a direct bond; or —X—R$^2$ is CN; R$^1$ is H, OH, halo, NH$_2$, mono- or di(C$_{1-4}$alkyl)NH$_2$, C$_{1-6}$alkyl, C$_{1-6}$alkylO, C$_{3-7}$cycloalkyl, aryl, arylC$_{1-6}$alkyl, NH$_2$C$_{1-4}$akyl, mono- or di(C$_{1-4}$alkyl)NH$_2$C$_{1-4}$akyl or mono- or di(C$_{1-4}$alkyl)NH$_2$C$_{1-4}$ alkylNH$_2$; R$^2$ is aryl, Het$^1$, optionally substituted C$_{3-7}$cycloalkyl, optionally substituted C$_{1-6}$alkyl; R$^3$ is H or C$_{1-4}$alkyl; R$^4$ and R$^5$ are —C(=O)—Z—R$^{14}$, C$_{1-6}$alkyl, halo, polyhaloC$_{1-6}$alkyl, OH, mercapto, C$_{1-6}$alkylO, C$_{1-6}$alkylthio, C$_{1-6}$alkylC(=O)O, aryl, cyano, nitro, Het$^3$, R$^6$, NR$^7$R$^8$ or C$_{1-4}$alkyl substituted with —C(=O)—Z—R$^{14}$, Het$^3$, R$^6$ or NR$^7$R$^8$; Z is O, S, NH, —CH$_2$O or —CH$_2$—S—; R$^{14}$ is H, C$_{1-20}$acyl, optionally substituted C$_{1-20}$alkyl, optionally substituted C$_{3-20}$alkenyl, C$_{3-20}$alkynyl, C$_{3-7}$cycloalkyl, polyhaloC$_{1-20}$alkyl, Het$^5$, phenyl; or R$^{14}$ is an oxygen containing radical; aryl is optionally substituted phenyl; Het$^1$, Het$^2$, Het$^3$ and Het$^5$ are optionally substituted heterocycles; Het$^4$ is a monocyclic heterocycle; provided however that R$^2$ is other than NH$_2$C(=O), C$_{1-6}$alkylOC(=O)C$_{1-6}$alkyl; and R$^{11}$ is other than COOH, C$_{1-4}$alkylOC(=O), NH$_2$C(=O), C$_{1-4}$alkylNH$_2$C(=O), OHC$_{1-4}$alkylNH$_2$C(=O), C$_{1-4}$alkylC(=O)NH$_2$C(=O), C$_{3-7}$cycloalkylNH$_2$C(=O); and R$^7$, R$^8$, R$^9$, R$^{10}$, R$^{12}$, R$^{13}$, R$^{15}$ and R$^{16}$ are other than C$_{1-4}$alkylC(=O)OC$_{1-4}$alkylC(=O), OHC$_{1-4}$alkylC(=O); and Het$^3$ is other than a monocyclic heterocycle substituted with COOH or C$_{1-4}$alkylOC(=O); and the compounds of formula (I) contain at least one —C(=O)—Z—R$^{14}$ moiety: to processes for their preparation and compositions comprising them. It further relates to their use as a medicine.

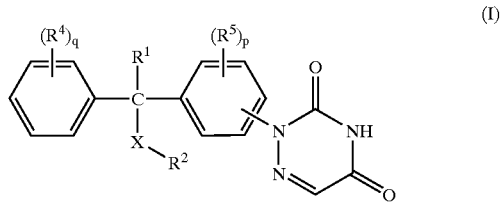

5 Claims, No Drawings

IL-5 INHIBITING 6-AZAURACIL DERIVATIVES

The present invention concerns novel IL-5 inhibiting 6-azauracil derivatives useful for treating eosinophil-dependent inflammatory diseases; to processes for their preparation and compositions comprising them. It further relates to their use as a medicine.

Eosinophil influx, leading to subsequent tissue damage, is an important pathogenic event in bronchial asthma and allergic diseases. The cytokine interleukin-5 (IL-5), produced mainly by T lymphocytes as a glycoprotein, induces the differentiation of eosinophils in bone marrow and, primes eosinophils for activation in peripheral blood and sustains their survival in tissues. As such, IL-5 plays a critical role in the process of eosinophilic inflammation. Hence, the possibility that inhibitors of IL-5 production would reduce the production, activation and/or survival of eosinophils provides a therapeutic approach to the treatment of bronchial asthma and allergic diseases such as, atopic dermatitis, allergic rhinitis, allergic conjunctivitis, and also other eosinophil-dependent inflammatory diseases.

Steroids, which strongly inhibit IL-5 production in vitro, have long been used as the only drugs with remarkable efficacy for bronchial asthma and atopic dermatitis, but they cause various serious adverse reactions such as diabetes, hypertension and cataracts. Therefore, it would be desirable to find non-steroidal compounds having the ability to inhibit IL-5 production in human T-cells and which have little or no adverse reactions.

U.S. Pat. No. 4,631,278 discloses α-aryl-4-(4,5-dihydro-3,5-dioxo-1,2,4-triazin-2(3H)-yl)-benzeneacetonitriles and U.S. Pat. No. 4,767,760 discloses 2-(substituted phenyl)-1,2,4-triazine-3,5(2H,4H)-diones, all having anti-protozoal activity, in particular, anti-coccidial activity. EP 831,088 discloses 1,2,4-triazine-3,5-diones as anticoccidial agents.

The present invention provides compounds which have never been described hitherto and which possess a remarkable pharmacological activity as inhibitors of the production of IL-5.

The present invention is concerned with the compounds of formula

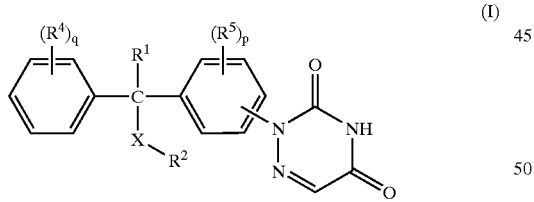

(I)

the N-oxides, the pharmaceutically acceptable addition salts, quaternary amines and the stereochemically isomeric forms thereof, wherein p represents an integer being 0, 1, 2, 3 or 4;
q represents an integer being 0, 1, 2, 3, 4 or 5;
X represents O, S, $NR^3$ or a direct bond; or
—X—$R^2$ taken together may represent cyano;
$R^1$ represents hydrogen, hydroxy, halo, amino, mono- or di($C_{1-4}$alkyl)amino, $C_{1-6}$alkyl, $C_{1-6}$alkyloxy, $C_{3-7}$cycloalkyl, aryl, aryl$C_{1-6}$alkyl, amino$C_{1-4}$alkyl, mono- or di($C_{1-4}$alkyl)amino$C_{1-4}$alkyl or mono- or di($C_{1-4}$alkyl)amino-$C_{1-4}$alkylamino;
$R^2$ represents aryl, $Het^1$, $C_{3-7}$cycloalkyl optionally substituted with —C(=O)—Z—$R^{14}$, $C_{1-6}$alkyl or $C_{1-6}$alkyl substituted with one or two substituents selected from hydroxy, cyano, amino, mono- or di($C_{1-4}$alkyl)amino, —C(=O)—Z—$R^{14}$, $C_{1-6}$alkyloxy optionally substituted with —C(=O)—Z—$R^{14}$, $C_{1-6}$alkylsulfonyloxy, $C_{3-7}$cycloalkyl optionally substituted with —C(=O)—Z—$R^{14}$, aryl, aryloxy, arylthio, $Het^1$, $Het^1$oxy and $Het^1$thio; and if X is O, S or $NR^3$, then $R^2$ may also represent —C(=O)—Z—$R^{14}$, aminothiocarbonyl, $C_{1-4}$alkylcarbonyl optionally substituted with —C(=O)—Z—$R^{14}$, $C_{1-4}$alkylthiocarbonyl optionally substituted with —C(=O)—Z—$R^{14}$, arylcarbonyl, arylthiocarbonyl, $Het^1$carbonyl or $Het^1$thiocarbonyl;
$R^3$ represents hydrogen or $C_{1-4}$alkyl;
each $R^4$ independently represents —C(=O)—Z—$R^{14}$, $C_{1-6}$alkyl, halo, polyhalo$C_{1-6}$alkyl, hydroxy, mercapto, $C_{1-6}$alkyloxy, $C_{1-6}$alkylthio, $C_{1-6}$alkylcarbonyloxy, aryl, cyano, nitro, $Het^3$, $R^6$, $NR^7R^8$ or $C_{1-4}$alkyl substituted with —C(=O)—Z—$R^{14}$, $Het^3$, $R^6$ or $NR^7R^8$;
each $R^5$ independently represents —C(=O)—Z—$R^{14}$, $C_{1-6}$alkyl, halo, polyhalo$C_{1-6}$alkyl, hydroxy, mercapto, $C_{1-6}$alkyloxy, $C_{1-6}$alkylthio, $C_{1-6}$alkylcarbonyloxy, aryl, cyano, nitro, $Het^3$, $R^6$, $NR^7R^8$ or $C_{1-4}$alkyl substituted with —C(=O)—Z—$R^{14}$, $Het^3$, $R^6$ or $NR^7R^8$;
each $R^6$ independently represents $C_{1-6}$alkylsulfonyl, aminosulfonyl, mono- or di-($C_{1-4}$alkyl)aminosulfonyl, mono- or di(benzyl)aminosulfonyl, polyhalo$C_{1-6}$alkylsulfonyl, $C_{1-6}$alkylsulfonyl, phenyl$C_{1-4}$alkylsulfonyl, piperazinylsulfonyl, piperidinyl-sulfonyl, aminopiperidinylsulfonyl, piperidinylaminosulfonyl, N-$C_{1-4}$alkyl-N-piperidinylaminosulfonyl or mono- or di($C_{1-4}$alkyl)amino$C_{1-4}$alkylsulfonyl;
each $R^7$ and each $R^8$ are independently selected from hydrogen, $C_{14}$alkyl, hydroxy-$C_{1-4}$alkyl, dihydroxy$C_{1-4}$alkyl, aryl, aryl$C_{1-4}$alkyl, $C_{1-4}$alkyloxy$C_{1-4}$alkyl, $C_{1-4}$alkyl-carbonyl, arylcarbonyl, $Het^3$carbonyl, —C(=O)—Z—$R^{14}$, mono- or di($C_{1-4}$alkyl)amino-$C)_4$alkyl, arylaminocarbonyl, arylaminothiocarbonyl, $Het^3$aminocarbonyl, $Het^3$amino-thiocarbonyl, $C_{3-7}$cycloalkyl, pyridinyl$C_{1-4}$alkyl, $C_{1-4}$alkanediyl-C(=O)—Z—$R^{14}$, —Y—$C_{1-4}$alkanediyl-C(=O)—Z—$R^{14}$, $Het^3$ and $R^6$; or $R^7$ and $R^8$ taken together with the nitrogen atom to which they are attached form a radical of formula

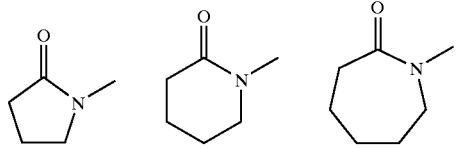

$R^9$ and $R^{10}$ are each independently selected from hydrogen, $C_{1-4}$alkyl, hydroxy$C_{1-4}$alkyl, dihydroxy$C_{1-4}$alkyl, phenyl, phenyl$C_{1-4}$alkyl, $C_{1-4}$alkyloxy$C_{1-4}$ alkyl, $C_{1-4}$alkyl-carbonyl, phenylcarbonyl, $Het^3$carbonyl, —C(=O)—Z—$R^{14}$, mono- or di($C_{1-4}$alkyl)amino-$C_{1-4}$ alkyl, phenylaminocarbonyl, phenylamino-thiocarbonyl, $Het^3$ aminocarbonyl, $Het^3$ aminothiocarbonyl, $C_{3-7}$cycloalkyl, pyridinyl$C_{1-4}$alkyl, $C_{1-4}$alkanediyl-C(=O)—Z—$R^{14}$, —Y—$C_{1-4}$ alkanediyl-C(=O)—Z—$R^{14}$, $Het^3$ and $R^6$; or $R^9$ and $R^{10}$ taken together with the nitrogen atom to which they are attached form a radical of formula

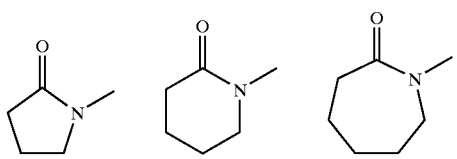

each $R^{11}$ independently being selected from hydroxy, mercapto, cyano, nitro, halo, —C(=O)—Z—$R^{14}$, —Y—$C_{1-4}$alkanediyl-C(=O)—Z—$R^{14}$, trihalomethyl, $C_{1-4}$alkyloxy optionally substituted with —C(=O)—Z—$R^{14}$, formyl, trihalo$C_{1-4}$alkylsulfonyloxy, $R^6$, $NR^7R^8$, C(=O)$NR^{15}$ $R^{16}$, aryl, aryloxy, arylcarbonyl, $C_{3-7}$cycloalkyl optionally substituted with —C(=O)—Z—$R^{14}$, $C_{3-7}$cycloalkyloxy optionally substituted with —C(=O)—Z—$R^{14}$, phthalimide-2-yl, $Het^3$, $Het^4$ and C(=O)$Het^3$;

$R^{12}$ and $R^{13}$ are each independently selected from hydrogen, $C_{1-4}$alkyl, hydroxy$C_{1-4}$alkyl, dihydroxy$C_{1-4}$alkyl, phenyl, phenyl$C_{1-4}$alkyl, $C_{1-4}$alkyloxy$C_{1-4}$alkyl, $C_{1-4}$alkyl-carbonyl, phenylcarbonyl, —C(=O)—Z—$R^{14}$, mono- or di($C_{1-4}$alkyl)amino$C_{1-4}$alkyl, phenylaminocarbonyl, phenylaminothiocarbonyl, $C_{3-7}$cycloalkyl, pyridinyl$C_{1-4}$alkyl, $C_{1-4}$alkanediyl-C(=O)—Z—$R^{14}$, —Y—$C_{1-4}$alkanediyl-C(=O)—Z—$R^{14}$ and $R^6$; or $R^9$ and $R^{10}$ taken together with the nitrogen atom to which they are attached form a radical of formula

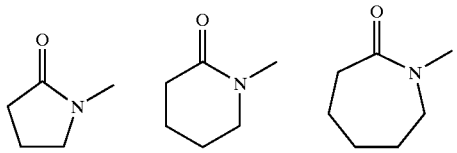

each Z independently represents O, S, NH, —$CH_2$—O— —$CH_2$—S— whereby —$CH_2$— is attached to the carbonyl group;

each $R^{14}$ independently represents hydrogen, $C_{1-20}$acyl (having a straight or branched, saturated or unsaturated hydrocarbon chain having 1 to 20 carbon atoms), $C_{1-20}$alkyl, $C_{3-20}$alkenyl optionally substituted with phenyl, $C_{3-20}$alkynyl, $C_{3-7}$cycloalkyl, polyhalo$C_{1-20}$alkyl, $Het^5$, phenyl or $C_{1-20}$alkyl substituted with one or more substituents selected from hydroxy, $NR^{17}$, $R^{18}$, phenyl, mono- or di($C_{1-4}$alkyl)amino, cyano, $Het^5$, $C_{1-4}$alkyloxycarbonyl, phenyl$C_{1-4}$alkyloxycarbonyl and $C_{3-7}$cycloalkyl; or $R^{14}$ represents a radical of formula (a)

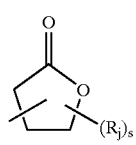

(b)

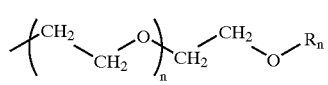

(c)

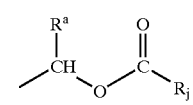

(d)

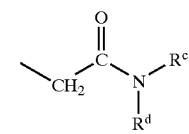

(e)

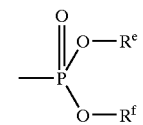

(h)

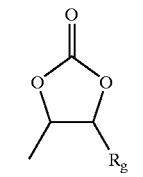

(i)

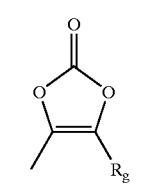

(d)

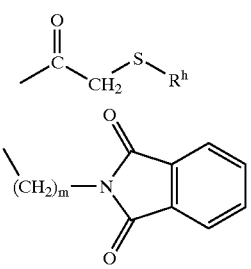

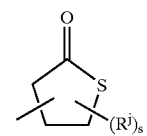

(l)

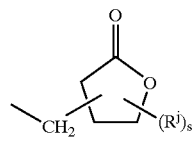

(m)

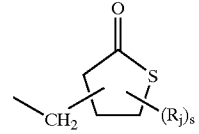

(n)

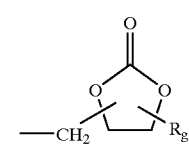

(o)

-continued

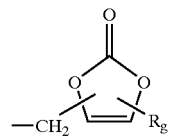 (p)

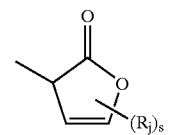 (q)

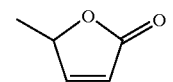 (r)

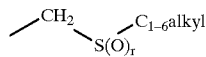 (s)

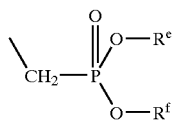 (e)

wherein n is 0 to 5; m is 1 to 4; s is zero to 4; r is 0 to 2;

$R^a$, $R^b$, $R^c$, $R^d$, $R^e$ and $R^f$ are each independently hydrogen, or $C_{1-6}$alkyl; phenyl or $C_{3-7}$cycloalkyl; or $R^e$ and $R^f$ taken together may form —CH$_2$—CH$_2$—, —CH$_2$—CH$_2$—CH$_2$— or —CH$_2$—CH$_2$—CH$_2$—CH$_2$—;

$R^g$, $R^h$ and $R^k$ are each independently hydrogen or $C_{1-4}$alkyl;

each $R^j$ independently is $C_{1-4}$alkyl;

$R^i$ is —O—$R^6$, $C_{1-6}$alkyl, phenyl or $C_{3-7}$cycloalkyl optionally substituted with $C_{1-4}$alkyloxy;

$R^n$ is hydrogen, $C_{1-4}$alkyl, phenyl, phenyl$C_{1-4}$alkyl or $C_{3-7}$cycloalkyl;

$R^m$ is hydrogen or $C_{1-4}$alkyloxy; or

—Z—$R^{14}$ taken together form a radical of formula

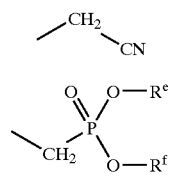 (f)

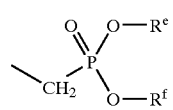 (g)

$R^{15}$ and $R^{16}$ are each independently selected from hydrogen, $C_{1-4}$alkyl, hydroxy$C_{1-4}$alkyl, dihydroxy$C_{1-4}$alkyl, aryl, aryl$C_{1-4}$alkyl, $C_{1-4}$alkyloxy$C_{1-4}$alkyl, —C(=O)Z—$R^{14}$, arylcarbonyl, mono- or di($C_{1-4}$alkyl)amino$C_{1-4}$alkyl, arylaminocarbonyl, arylamino-10 thiocarbonyl, aminocarbonylmethylene, mono- or di($C_{1-4}$alkyl)aminocarbonyl-methylene, Het$^3$aminocarbonyl, Het$^3$aminothiocarbonyl, pyridinyl$C_{1-4}$alkyl, Het$^3$ or $R^6$; or $R^{15}$ and $R^{16}$ taken together with the nitrogen atom to which they are attached form a radical of formula

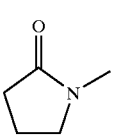 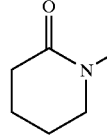 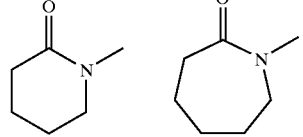

$R^{17}$ and $R^{18}$ are each independently selected from hydrogen, $C_{1-4}$alkyl, hydroxy$C_{1-4}$alkyl, dihydroxy$C_{1-4}$akyl, phenyl, phenyl$C_{1-4}$alkyl, $C_{1-4}$alkyloxy$C_{1-4}$alkyl, $C_{1-4}$alkyl-carbonyl, phenylcarbonyl, mono- or di($C_{1-4}$alkyl)amino$C_{1-4}$alkyl, phenylamino-carbonyl, phenylaminothiocarbonyl, $C_{3-7}$cycloalkyl, pyridinyl$C_{1-4}$alkyl, $C_{1-4}$alkanediyl-C(=O)—Z—$C_{1-6}$alkyl, —C(=O)—Z—$C_{1-6}$alkyl, —Y—$C_{1-4}$alkanediyl-C(=O)—Z—$C_{1-6}$alkyl and $R^6$;

aryl represents phenyl optionally substituted with one, two or three substituents each independently selected from nitro, azido, cyano, halo, hydroxy, $C_{1-4}$alkyl, $C_{3-7}$cycloalkyl, $C_{1-4}$alkyloxy, formyl, polyhalo$C_{1-4}$alkyl, NR$^9$R$^{10}$, —C(=O)NR$^9$R$^{10}$, —C(=O)—Z—R$^{14}$, $R^6$, —O—$R^6$; phenyl, Het$^3$, C(=O)Het$^3$, and $C_{1-4}$alkyl substituted with one or more substituents each independently selected from halo, hydroxy, $C_{1-4}$alkyloxy, —C(=O)—Z—R$^{14}$, —Y—$C_{1-4}$alkanediyl-C(=O)—Z—R$^{14}$, Het$^3$ or NR$^9$R$^{10}$;

Het$^1$ represents a heterocycle selected from pyrrolyl, pyrrolinyl, imidazolyl, imidazo-linyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, pyrrolidinyl, piperidinyl, piperazinyl, morpholinyl, thiomorpholinyl, dioxanyl, dithianyl, trithianyl, triazinyl, benzothienyl, isobenzothienyl, benzofuranyl, isobenzofuranyl, benzothiazolyl, benzoxazolyl, benzodioxanyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl, imidazo[2,1-b]thiazolyl; wherein said heterocycles each independently may optionally be substituted with one, or where possible, two or three substituents each independently selected from Het$^2$, R$^{11}$ and $C_{1-4}$alkyl optionally substituted with one or two substituents independently selected from Het$^2$ and R$^{11}$;

Het$^2$ represents a heterocycle selected from pyrrolyl, pyrrolinyl, imidazolyl, imidazo-linyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may optionally be substituted with one, or where possible, two or three substituents each independently selected from $R^{11}$ and $C_{1-4}$alkyl optionally substituted with one or two substituents each independently selected from $R^{11}$;

Het$^3$ represents a monocyclic heterocycle selected from azetidinyl, pyrrolidinyl, piperidinyl, piperazinyl, morpholinyl, thiomorpholinyl and tetrahydropyranyl; wherein said monocyclic heterocycles each independently may optionally be substituted with, where possible, one, two, three or four substituents each independently selected from hydroxy, $C_{1-4}$alkyl, $C_{1-4}$alkyloxy, —C(=O)—Z—$R^{14}$, $C_{1-4}$alkylcarbonyl, phenyl$C_{1-4}$alkyl, piperidinyl, $NR^{12}R^{13}$, $R^6$ and $C_{1-4}$alkyl substituted with one or two substituents each independently selected from hydroxy, $C_{1-4}$alkyloxy, phenyl, —Y—$C_{1-4}$alkanediyl-C(=O)—Z—$R^{14}$, —C(=O)—Z—$R^4$, $R^6$ or $NR^{12}R^{13}$;

Het$^4$ represents a monocyclic heterocycle selected from pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl;

Het$^5$ represents a heterocycle selected from pyrrolyl, pyrrolinyl, imidazolyl, imidazo-linyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, pyrrolidinyl, piperidinyl, piperazinyl, morpholinyl, thiomorpholinyl, tetrahydropyranyl, dioxanyl, dithianyl, trithianyl, triazinyl, benzothienyl, isobenzothienyl, benzofuranyl, isobenzofuranyl, benzothiazolyl, benzoxazolyl, benzodioxanyl, indolyl, isoindolyl, indolinyl, purinyl, 1H-pyrazolo[3,4-d]pyrimidinyl, benzimida-zolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may optionally be substituted with one, or where possible, two, three or four substituents each independently selected from hydroxy, $C_{1-4}$alkyl, $C_{1-4}$alkyloxy, $C_{1-4}$alkylcarbonyl, piperidinyl, $NR^{17}R^{18}$, C(=O)—Z—$C_{1-6}$alkyl, $R^6$, sulfonamido and $C_{1-4}$alkyl substituted with one or two substituents independently selected from hydroxy, $C_{1-4}$alkyloxy, phenyl, C(=O)—Z—$C_{1-6}$alkyl, —Y—$C_{1-6}$alkanediyl—C(=O)—Z—$C_{1-6}$alkyl, $R^6$ and $NR^{17}R^{18}$;

provided however that $R^2$ is other than aminocarbonyl, $C_{1-6}$alkyloxycarbonyl$C_{1-6}$alkyl; and $R^{11}$ is other than carboxyl, $C_{1-4}$alkyloxycarbonyl, aminocarbonyl, $C_{1-4}$alkylaminocarbonyl, hydroxy$C_{1-4}$alkylaminocarbonyl, $C_{1-4}$alkylcarbonylaminocarbonyl, $C_{3-7}$cycloalkylaminocarbonyl; and $R^7$, $R^8$, $R^9$, $R^{10}$, $R^{12}$, $R^{13}$, $R^{15}$ and $R^{16}$ are other than $C_{1-4}$alkylcarbonyloxy$C_{1-4}$alkylcarbonyl, hydroxy$C_{1-4}$ alkylcarbonyl; and Het$^3$ is other than a monocyclic heterocycle substituted with carboxyl or $C_{1-4}$alkyloxycarbonyl; and the compounds of formula (I) contain at least one —C(=O)—Z—$R^{14}$ moiety.

A special group of compounds are those compounds of formula (I) wherein

R represents aryl, Het$^1$, $C_{3-7}$cycloalkyl optionally substituted with —C(=O)—Z—$R^{14}$, $C_{1-6}$alkyl or $C_{1-6}$alkyl substituted with one or two substituents selected from hydroxy, cyano, amino, mono- or di($C_{1-4}$alkyl)amino, —C(=O)—Z—$R^{14}$, $C_{1-6}$alkyloxy optionally substituted with —C(=O)—Z—$R^{14}$, $C_{1-6}$alkylsulfonyloxy, $C_{3-7}$cycloalkyl optionally substituted with —C(=O)—Z—$R^{14}$, aryl, aryloxy, arylthio, Het$^1$, Het$^1$oxy and Het$^1$thio; and if X is O, S or $NR^3$, then $R^2$ may also represent —C(=O)—Z—$R^{14}$, aminothiocarbonyl, $C_{1-4}$alkylcarbonyl optionally substituted with —C(=O)—Z—$R^{14}$, $C_{1-4}$alkylthiocarbonyl optionally substituted with —C(=O)—Z—$R^{14}$, arylcarbonyl, arylthiocarbonyl;

each $R^6$ independently represents $C_{1-6}$alkylsulfonyl, aminosulfonyl, mono- or di($C_{1-4}$alkyl)aminosulfonyl, mono or di(benzyl)aminosulfonyl, polyhalo$C_{1-6}$alkylsulfonyl, $C_{1-6}$alkylsulfonyl, phenyl$C_{1-4}$alkylsulfonyl, piperazinylsulfonyl, aminopiperidinylsulfonyl, piperidinylaminosulfonyl, N-$C_{1-4}$alkyl-N-piperidinylaminosulfonyl;

each $R^7$ and each $R^8$ are independently selected from hydrogen, $C_{1-4}$alkyl, hydroxy-$C_{1-4}$alkyl, dihydroxy$C_{1-4}$ alkyl, aryl, aryl$C_{1-4}$alkyl, $C_{1-4}$alkyloxy$C_{1-4}$alkyl, $C_{1-4}$alkyl-carbonyl, arylcarbonyl, —C(=O)—Z—$R^{14}$, mono- or di($C_{1-4}$alkyl)amino$C_{1-4}$alkyl, arylaminocarbonyl, arylaminothiocarbonyl, Het$^3$aminocarbonyl, Het$^3$aminothiocarbonyl, $C_{3-7}$cycloalkyl, pyridinyl$C_{1-4}$alkyl, Het$^3$ and $R^6$;

$R^9$ and $R^{10}$ are each independently selected from hydrogen, $C_{1-4}$alkyl, hydroxy$C_{1-4}$alkyl, dihydroxy$C_{1-4}$ alkyl, phenyl, phenyl$C_{1-4}$alkyl, $C_{1-4}$alkyloxy$C_{1-4}$alkyl, $C_{1-4}$alkyl-carbonyl, phenylcarbonyl, —C(=O)—Z—$R^{14}$, mono- or di($C_{1-4}$alkyl)amino$C_{1-4}$alkyl, phenylaminocarbonyl, phenylaminothiocarbonyl, Het$^3$aminocarbonyl, Het$^3$aminothiocarbonyl, $C_{3-7}$cycloalkyl, pyridinyl$C_{1-4}$alkyl, Het$^3$ and $R^6$;

each $R^{11}$ independently being selected from hydroxy, mercapto, cyano, nitro, halo, —C(=O)—Z—$R^{14}$, trihalomethyl, $C_{1-4}$alkyloxy optionally substituted with —C(=O)—Z—$R^{14}$, formyl, trihalo$C_{1-4}$alkylsulfonyloxy, $R^6$, $NR^7R^8$, C(=O)$NR^{15}R^{16}$, aryl, aryloxy, arylcarbonyl, $C_{3-7}$cycloalkyl optionally substituted with —C(=O)—Z—$R^{14}$, $C_{3-7}$cycloalkyloxy optionally substituted with —C(=O)—Z—$R^{14}$, phthalimide-2-yl, Het$^3$ and C(=O)Het$^3$;

$R^{12}$ and $R^{13}$ are each independently selected from hydrogen, $C_{1-4}$alkyl, hydroxy$C_{1-4}$alkyl, dihydroxy$C_{1-4}$ alkyl, phenyl, phenyl$C_{1-4}$alkyl, $C_{1-4}$alkyloxy$C_{1-4}$alkyl, $C_{1-4}$alkyl-carbonyl, phenylcarbonyl, —C(=O)—Z—$R^{14}$, mono- or di($C_{1-4}$alkyl)amino$C_{1-4}$alkyl, phenylaminocarbonyl, phenylaminothiocarbonyl, $C_{3-7}$cycloalkyl, pyridinyl$C_{1-4}$alkyl and $R^6$;

each $R^{14}$ independently represents hydrogen, $C_{1-20}$acyl (having a straight or branched, saturated or unsaturated hydrocarbon chain having 1 to 20 carbon atoms), $C_{1-20}$alkyl, $C_{3-7}$cycloalkyl, polyhalo$C_{1-20}$alkyl; or $R^{14}$ represents a radical of formula (a)

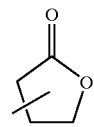

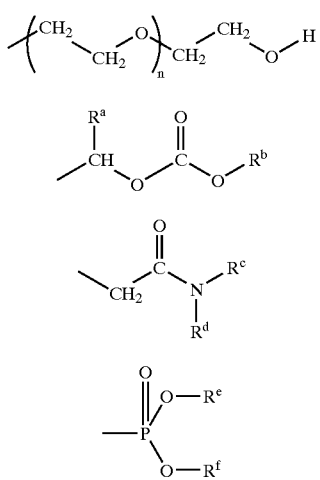

$R^a$, $R^b$, $R^c$, $R^d$, $R^e$ and $R^f$ are each independently hydrogen, $C_{1-6}$alkyl or $C_{3-7}$cycloalkyl; or $R^e$ and $R^f$ taken together may form —CH$_2$—CH$_2$—, —CH$_2$—CH$_2$—CH$_2$— or —CH$_2$—CH$_2$—CH$_2$—CH$_2$—;

$R^{15}$ and $R^{16}$ are each independently selected from dihydroxyC$_{1-4}$alkyl, aryl, arylC$_{1-4}$alkyl, C$_{1-4}$alkyloxyC$_{1-4}$alkyl, —C(=O)—Z—R$^{14}$, arylcarbonyl, mono- or di(C$_{1-4}$alkyl)-aminoC$_{1-4}$alkyl, arylaminocarbonyl, arylaminothiocarbonyl, Het$^3$aminocarbonyl, Het$^3$aminothiocarbonyl, pyridinylC$_{1-4}$alkyl, Het$^3$ or R$^6$;

aryl represents phenyl optionally substituted with one, two or three substituents each independently selected from nitro, azido, halo, hydroxy, C$_{1-4}$alkyl, C$_{1-4}$alkyloxy, polyhaloC$_{1-4}$alkyl, NR$^9$R$^{10}$, —C(=O)—Z—R$^{14}$, R$^6$, phenyl, Het$^3$, and C$_{1-4}$alkyl substituted with —C(=O)—Z—R$^{14}$ or NR$^9$R$^{10}$;

Het$^1$ represents a heterocycle selected from pyrrolyl, pyrrolinyl, imidazolyl, imidazo-linyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyrdazinyl, pyrrolidinyl, piperidinyl, piperazinyl, morpholinyl, thiomorpholinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl, imidazo[2,1-b]thiazolyl; wherein said heterocycles each independently may optionally be substituted with one, or where possible, two or three substituents each independently selected from Het$^2$, R$^{11}$ and C$_{1-4}$alkyl optionally substituted with Het$^2$ and R$^{11}$;

Het$^2$ represents a heterocycle selected from pyrrolyl, pyrrolinyl, imidazolyl, imidazo-linyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, dioxanyl, dithianyl, trithianyl, triazinyl; wherein said heterocycles each independently may optionally be substituted with one, or where possible, two or three substituents each independently selected from R$^{11}$ and C$_{1-4}$alkyl optionally substituted with R$^{11}$;

Het$^3$ represents a monocyclic heterocycle selected from pyrrolidinyl, piperidinyl, piperazinyl, morpholinyl, thiomorpholinyl; wherein said monocyclic heterocycles each independently may optionally be substituted with, where possible, one, two, substituents each independently selected from C$_{1-4}$alkyl, C$_{1-4}$alkyloxy, —C(=O)—Z—R$^{14}$, C$_{1-4}$alkylcarbonyl, phenylC$_{1-4}$alkyl, piperidinyl, NR$^{12}$R$^{13}$, R$^6$ and C$_{1-4}$alkyl substituted with —C(=O)—Z—R$^{14}$, R$^6$ or NR$^{12}$R$^{13}$.

As used in the foregoing definitions and hereinafter, halo is generic to fluoro, chloro, bromo and iodo; $C_{3-7}$cycloalkyl is generic to cyclopropyl, cyclobutyl, cyclopentyl, cyclohexyl and cycloheptyl; $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like; $C_{1-6}$alkyl is meant to include $C_{1-4}$alkyl and the higher homologues thereof having 5 or 6 carbon atoms such as, for example, pentyl, 2-methylbutyl, hexyl, 2-methylpentyl and the like $C_{1-20}$alkyl is meant to include $C_{1-6}$alkyl and the higher homologues thereof having 7 to 20 carbon atoms such as, for example, heptyl, octyl, nonyl, decyl, undecyl, dodecyl, tridecyl, tetradecyl, pentadecyl, octadecyl, nonadecyl, eicosyl and the like $C_{5-20}$alkyl is meant to include $C_{1-20}$alkyl except for $C_{1-4}$alkyl; polyhaloC$_{1-4}$alkyl is defined as polyhalosubstituted $C_{1-4}$alkyl, in particular $C_{1-4}$alkyl substituted with 1 to 6 halogen atoms, more in particular difluoro- or trifluoromethyl; polyhaloC$_{1-6}$alkyl is defined as polyhalosubstituted $C_{1-6}$alkyl; polyhaloC$_{1-20}$alkyl is defined as polyhalosubstituted $C_{1-20}$alkyl. The term $C_{1-4}$alkanediyl defines bivalent straight or branch chained alkanediyl radicals having from 1 to 4 carbon atoms such as, for example, methylene, 1,2-ethanediyl, 1,3-propanediyl, 1,4-butanediyl and the like; $C_{2-6}$alkanediyl defines bivalent straight or branch chained alkanediyl radicals having from 2 to 6 carbon atoms such as, for example, 1,2-ethanediyl, 1,3-propanediyl, 1,4-butanediyl, 1,5-pentanediyl, 1,6-hexanediyl and the like. The term $C_{3-20}$alkenyl defines straight and branched chain hydrocarbon radicals containing one double bond and having from 3 to 20 carbon atoms such as, for example, 2-propenyl, 3-butenyl, 2-butenyl, 2-pentenyl, 3-pentenyl, 3-methyl-2-butenyl, 3-hexenyl and the like; and the carbon of said $C_{3-20}$alkenyl connected to the remainder of the molecule preferably is saturated; and the term $C_{3-20}$alkynyl defines straight and branched chain hydrocarbon radicals containing one triple bond and having from 3 to 20 carbon atoms such as, for example, 2-propynyl, 3-butynyl, 2-butynyl, 2-pentynyl, 3-pentynyl, 3-methyl-2-butynyl, 3-hexynyl and the like; and the carbon of said $C_{3-20}$alkynyl connected to the remainder of the molecule preferably is saturated.

Het$^1$, Het$^2$, Het$^3$, Het$^4$ and Het$^5$ are meant to include all the possible isomeric forms of the heterocycles mentioned in the definition of Het$^1$, Het$^2$, Het$^3$, Het$^4$ or Het$^5$, for instance, pyrrolyl also includes 2H-pyrrolyl; triazolyl includes 1,2,4-triazolyl and 1,3,4-triazolyl; oxadiazolyl includes 1,2,3-oxadiazolyl, 1,2,4-oxadiazolyl, 1,2,5-oxadiazolyl and 1,3,4-oxadiazolyl; thiadiazolyl includes 1,2,3-thiadiazolyl, 1,2,4-thiadiazolyl, 1,2,5-thiadiazolyl and 1,3,4-thiadiazolyl; pyranyl includes 2H-pyranyl and 4H-pyranyl.

The heterocycles represented by Het$^1$, Het$^2$, Het$^3$, Het$^4$ and Het$^5$ may be attached to the remainder of the molecule of formula (I) through any ring carbon or heteroatom as appropriate. Thus, for example, when the heterocycle is imidazolyl, it may be a 1-imidazolyl, 2-imidazolyl, 4-imidazolyl and 5-imidazolyl; when it is thiazolyl, it may be 2-thiazolyl, 4-thiazolyl and 5-thiazolyl; when it is triazolyl, it may be 1,2,4-triazol-1-yl, 1,2,4-triazol-3-yl, 1,2,4-triazol-5-yl, 1,3,4-triazol-1-yl and 1,3,4-triazol-2-yl; when it is benzthiazolyl, it may be 2-benzthiazolyl, 4-benzthiazolyl, 5-benzthiazolyl, 6-benzthiazolyl and 7-benzthiazolyl.

The $C_{1-20}$acyl is derived from

| acetic acid | $CH_3COOH$ | tridecanoic acid | $C_{12}H_{25}COOH$ |
| propionic acid | $C_2H_5COOH$ | myristic acid | $C_{13}H_{27}COOH$ |
| butyric acid | $C_3H_7COOH$ | pentadecanoic acid | $C_{14}H_{29}COOH$ |
| valeric acid | $C_4H_9COOH$ | palmitic acid | $C_{15}H_{31}COOH$ |
| hexanoic acid | $C_5H_{11}COOH$ | heptadecanoic acid | $C_{16}H_{33}COOH$ |
| heptanoic acid | $C_6H_{13}COOH$ | stearic acid | $C_{17}H_{35}COOH$ |
| octanoic acid | $C_7H_{15}COOH$ | oleic acid | $C_{17}H_{33}COOH$ |
| nonanoic acid | $C_8H_{17}COOH$ | linolic acid | $C_{17}H_{31}COOH$ |
| decanoic acid | $C_9H_{19}COOH$ | linolenic acid | $C_{17}H_{29}COOH$ |
| undecanoic acid | $C_{10}H_{21}COOH$ | nonadecanoic acid | $C_{18}H_{37}COOH$ |
| lauric acid | $C_{11}H_{23}COOH$ | icosanoic acid | $C_{19}H_{39}COOH$ |

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxy-acetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulphonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, 2-amino-2-(hydroxymethyl)-1,3-propanediol, hydrabamine salts, and salts with amino acids such as, for example, arginine, lysine, choline and the like. Conversely the salt form can be converted by treatment with acid into the free acid form.

The term addition salt also comprises the hydrates and solvent addition forms which the compounds of formula (I) are able to form. Examples of such forms are e.g. hydrates, alcoholates and the like.

The N-oxide forms of the present compounds are meant to comprise the compounds of formula (I) wherein one or several nitrogen atoms are oxidized to the so-called N-oxide. For example, one or more nitrogen atoms of any of the heterocycles in the definition of $Het^1$, $Het^2$, $Het^3$, $Het^4$ and $Het^5$ may be N-oxidised.

Some of the compounds of formula (I) may also exist in their tautomeric forms. Such forms although not explicitly indicated in the above formula are intended to be included within the scope of the present invention. For example, a hydroxy substituted triazine moiety may also exist as the corresponding triazinone moiety; a hydroxy substituted pyrimidine moiety may also exist as the corresponding pyrimidinone moiety.

The term "stereochemically isomeric forms" as used hereinbefore defines all the possible stereoisomeric forms in which the compounds of formula (I) can exist. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centres may have the R- or S-configuration, used herein in accordance with Chemical Abstracts nomenclature. Stereochemically isomeric forms of the compounds of formula (I) are obviously intended to be embraced within the scope of this invention.

The compounds of formula (I) and some of the intermediates in the present invention contain one or more asymmetric carbon atoms. The pure and mixed stereochemically isomeric forms of the comppounds of formula (I) are intended to be embraced within the scope of the present invention.

Whenever used hereinafter, the term "compounds of formula (I)" is meant to also include their N-oxide forms, their pharmaceutically acceptable addition salts, quaternary amines and their stereochemically isomeric forms.

The numbering of the phenyl ring bearing substituent $R^4$ is given hereinbelow and is used herein as such when indicating the position of the $R^4$ substituents on said phenyl ring, unless otherwise indicated.

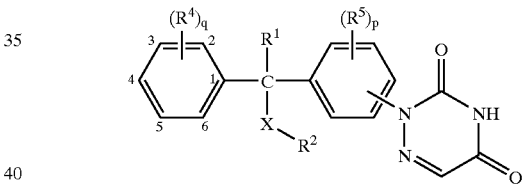

The carbon atom bearing the two phenyl rings and the $R^1$ and —X—$R^2$ substituents will be referred herein as the central carbon atom.

An interesting group of compounds are those compounds of formula (I) wherein the 6-azauracil moiety is connected to the phenyl ring in the para or meta position relative to the central carbon atom; preferably in the para position.

Another interesting group contains those compounds of formula (I) wherein one or more of the following restrictions apply:

p is 0, 1 or 2;

X is S, $NR^3$, or a direct bond; more in particular NH or a direct bond;

each $R^5$ independently is halo, polyhalo$C_{1-6}$alkyl, $C_{1-6}$alkyl, $C_{1-6}$alkyloxy or aryl, preferably, chloro or trifluoromethyl, more preferably chloro;

the at least one —C(=O)—Z—$R^{14}$ moiety contained by the compound of formula (I) is born by $R^2$;

$R^2$ is $Het^1$ or $C_{1-6}$alkyl substituted with one or two substituents selected from hydroxy, cyano, amino, mono- or di($C_{1-4}$alkyl)amino, C(=O)—Z—$R^{14}$ $C_{1-6}$alkyloxy optionally substituted with C(=O)—Z—$R^{14}$, $C_{1-6}$alkylsulfonyloxy, $C_{3-7}$cycloalkyl optionally substituted with C(=O)—Z—$R^{14}$, aryl, aryloxy, arylthio, $Het^1$, $Het^1$oxy and $Het^1$thio; and if X is O, S or NR, then $R^2$ may also represent aminothiocarbonyl, $C_{1-4}$alkylcarbonyl optionally substituted with C(=O)—Z—$R^{14}$, $C_{1-4}$alkylthiocarbonyl optionally substituted with C(=O)—Z—$R^{14}$, arylcarbonyl, arylthiocarbonyl, $Het^1$carbonyl or $Het^1$thiocarbonyl; particularly $R^2$ is $Het^1$ or in the event X is NH, $R^2$ may also be aminothiocarbonyl or $Het^1$carbonyl;

$R^1$ is hydrogen or methyl; preferably, methyl;

$R^6$ is $C_{1-6}$alkylsulfonyl or aminosulfonyl;

$R^7$ and $R^8$ are each independently hydrogen, $C_{1-4}$alkyl, $Het^3$ or $R^6$;

$R^9$ and $R^{10}$ are each independently hydrogen, $C_{1-4}$alkyloxy$C_{1-4}$alkyl, $C_{1-4}$alkylcarbonyl, aminocarbonyl, $Het^3$carbonyl, $Het^3$ or $R^6$;

$R^{11}$ is cyano, nitro halo, $C_{1-4}$alkyloxy, formyl, $NR^7R^8$, C(=O)$NR^{15}R^{16}$, —C(=O)—Z—$R^{14}$, aryl, arylcarbonyl, $Het^3$, $Het^4$ or C(=O)$Het^3$; more preferably $R^{11}$ is phenyl, —C(=O)—O—$R^{14}$, —C(=O)—S—$R^{14}$, or, —C(=O)—NH—$R^{14}$;

$R^{14}$ is dihydrofuranyl, $C_{5-20}$alkyl, $C_{3-20}$alkenyl, polyhalo$C_{1-6}$alkyl, $Het^5$ or $C_{1-20}$alkyl substituted with one or more substituents selected from phenyl, $C_{1-4}$alkylamino, cyano, $Het^1$, hydroxy and $C_{3-7}$cycloalkyl;

$R^{17}$ and $R^{18}$ are each independently hydrogen or phenyl;

aryl is phenyl optionally substituted with one, two or three substituents each independently selected from nitro, cyano, halo, hydroxy, $C_{1-4}$alkyl, $C_{3-7}$cycloalkyl, $C_{1-4}$alkyloxy, formyl, polyhalo$C_{1-4}$alkyl, $NR^9R^{10}$, C(=O)$NR^9R^{10}$, C(=O)—O—$R^{14}$, —O—$R^6$, phenyl, C(=O)$Het^3$ and $C_{1-4}$alkyl substituted with one or more substituents each independently selected from halo, hydroxy, $C_{1-4}$alkyloxy, C(=O)—Z—$R^{14}$, $Het^3$ or $NR^9R^{10}$;

$Het^1$ is a monocyclic heterocycle selected from pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, in particular imidazolyl, oxadiazolyl, thiazolyl, pyrimidinyl or pyridinyl, wherein said monocyclic heterocycles each independently may optionally be substituted with one, or where possible, two or three substituents each independently selected from $Het^2$, $R^{11}$ and $C_{1-4}$akyl optionally substituted with $Het^2$ or $R^{11}$; preferably $Het^1$ is imidazolyl, oxadiazolyl, thiazolyl or pyridinyl each independently and optionally substituted with one, or where possible, two or three substituents each independently selected from $Het^2$, $R^{11}$ and $C_{1-4}$alkyl optionally substituted with $Het^2$ or $R^{11}$;

$Het^2$ is an aromatic heterocycle; more in particular furanyl, thienyl, pyridinyl or benzothienyl, wherein said aromatic heterocycles each independently may optionally be substituted with one, or where possible, two or three substituents each independently selected from $R^{11}$ and $C_{1-4}$alkyl; :

$Het^3$ is azetidinyl, piperidinyl, piperazinyl, morpholinyl and tetrahydropyranyl each independently and optionally substituted with, where possible, one, two, three or four substituents each independently selected from hydroxy, $C_{1-4}$alkyl, $C_{1-4}$alkylcarbonyl, piperidinyl and $C_{1-4}$alkyl substituted with one or two substituents independently selected from hydroxy, $C_{1-4}$alkyloxy and phenyl;

$Het^4$ is thienyl;

$Het^5$ is piperidinyl or piperazinyl optionally substituted with $C_{1-4}$alkyl or sulfonamido.

Suitably, $Het^1$ represents a heterocycle selected from imidazolyl, triazolyl, furanyl, oxazolyl, thiazolyl, thiazolinyl, thiadiazolyl, oxadiazolyl, pyridinyl, pyrimidinyl, pyrazinyl, piperidinyl, piperazinyl, triazinyl, benzothiazolyl, benzoxazolyl, purinyl, 1H-pyrazolo-[3,4-d]pyrimidinyl, benzimidazolyl, thiazolopyridinyl, oxazolopyridinyl, imidazo-[2,1-b]thiazolyl; wherein said heterocycles each independently may optionally be substituted with one, or where possible, two or three substituents each independently selected from $Het^2$, $R^{11}$ and $C_{1-4}$alkyl optionally substituted with $Het^2$ or $R^{11}$. Suitably, $Het^2$ represents furanyl, thienyl or pyridinyl; wherein said monocyclic heterocycles each independently may optionally be substituted with $C_{1-4}$alkyl. Suitably, $Het^3$ represents pyrrolidinyl, piperidinyl, piperazinyl, morpholinyl, thiomorpholinyl; wherein said monocyclic heterocycles each independently may optionally be substituted with, where possible, one, two or three substituents each independently selected from $C_{1-4}$alkyl, $C_{1-4}$alkyloxy, —C(=O)—Z—$R^{14}$, $C_{1-4}$alkylcarbonyl, phenyl$C_{1-4}$alkyl, piperidinyl, $NR^{12}R^{13}$ and $C_{1-4}$alkyl substituted with —C(=O)—Z—$R^{14}$ or $NR^{12}R^{13}$.

Particular compounds are those compounds of formula (I) wherein $R^4$ and $R^5$ each independently are —C(=O)—Z—$R^{14}$, halo, polyhalo$C_{1-6}$alkyl, $C_{1-6}$alkyl optionally substituted with —C(=O)—$Z_7R^{14}$, $C_{1-6}$alkyloxy or aryl, more in particular, chloro or trifluoromethyl.

Other particular compounds are those compounds of formula (I) wherein $R^2$ represents aryl, $Het^1$, $C_{3-7}$cycloalkyl optionally substituted with —C(=O)—Z—$R^{14}$ or $C_{1-6}$alkyl substituted with one or two substituents selected from hydroxy, cyano, amino, mono- or di($C_{1-4}$alkyl)amino, $C_{1-6}$alkyloxy, $C_{1-6}$alkylsulfonyloxy, $C_{1-6}$alkyloxycarbonyl, $C_{3-7}$cycloalkyl, aryl, aryloxy, arylthio, $Het^1$, $Het^1$oxy and $Het^1$thio; and if X is O, S or $NR^3$, then $R^2$ may also represent —C(=O)—Z—$R^{14}$, aminothiocarbonyl, $CC_{1-4}$alkylcarbonyl, $C_{1-4}$alkylthiocarbonyl, arylcarbonyl or arylthiocarbonyl; more in particular $R^2$ is oxadiazolyl, thiazolyl, pyrimidinyl or pyridinyl; wherein said heterocycles each independently may optionally be substituted with one, or where possible, two or three substituents each independently selected from $Het^2$, $R^{11}$ and $C_{1-4}$alkyl optionally substituted with $Het^2$ or $R^{11}$.

Yet other particular compounds are those compounds of formula (I) wherein X is O, S, NH or a direct bond, more preferably S or a direct bond, most preferably a direct bond.

Preferred compounds are those compounds of formula (I) wherein q is 1 or 2 and one $R^4$ substituent, preferably chloro, is in the 4 position.

Other preferred compounds are those compounds of formula (I) wherein p is 1 or 2 and the one or two $R^5$ substituents, preferably chloro, are in the ortho position relative to the central carbon atom.

In order to simplify the structural representation of the compounds of formula (I), the group

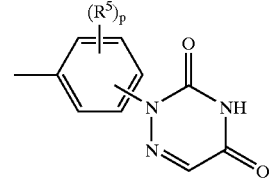

will hereinafter be represented by the symbol D.

Compounds of formula (I) can generally be prepared by reacting an intermediate of formula (I) wherein $W^1$ is a suitable leaving group such as, for example, a halogen atom, with an appropriate reagent of formula (III).

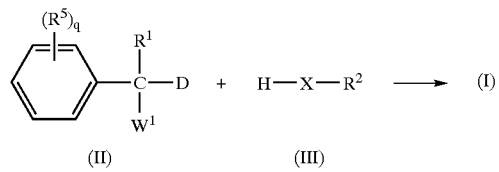

Said reaction may be performed in a reaction-inert solvent such as, for example, acetonitrile, N,N-dimethylformamide, acetic acid, tetrahydrofuran, ethanol or a mixture thereof. Alternatively, in case the reagent of formula (III) acts as a solvent, no additional reaction-inert solvent is required. The reaction is optionally carried out in the presence of a base such as, for example, 1,8-diazabicyclo[5.4.0]undec-7-ene, sodium bicarbonate, sodiumethanolate and the like. Convenient reaction temperatures range between $-70°$ C. and reflux temperature.

In this and the following preparations, the reaction products may be isolated from the reaction medium and, if necessary, further purified according to methodologies generally known in the art such as, for example, extraction, crystallisation, distillation, trituration and chromatography.

Alternatively, compounds of formula (I) may generally be prepared by cyclising an intermediate of formula (IV) wherein L is a suitable leaving group such as, for example, $C_{1-6}$alkyloxy or halo, and E represents an appropriate electron attracting group such as, for example, an ester, an amide, a cyanide, $C_{1-6}$alkylsulfonyloxy and the like groups; and eliminating the group E of the thus obtained triazinedione of formula (V). Said reaction procedure is analogous to the one described in EP-A-0,170,316.

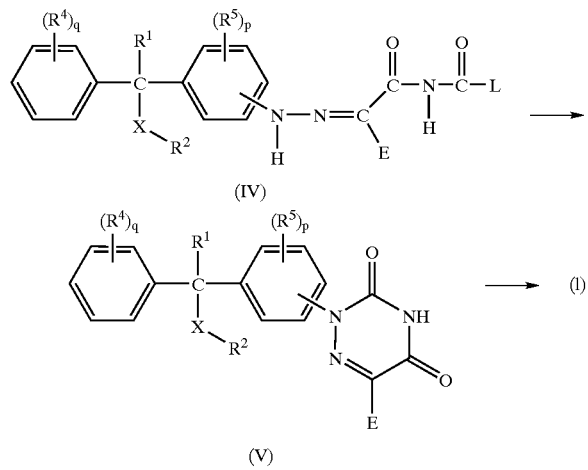

Some of the compounds and intermediates of the present invention can be prepared according to or analogous to the procedures described in EP-A-0,170,316 and EP-A-0,232,932.

For instance, scheme 1 depicts a reaction pathway for the preparation of compounds of formula (I) wherein $R^1$ is hydrogen and X is a direct bond, said compounds being represented by formula (I-a-1). A ketone of formula (VI) can be reacted with a reagent of formula (VII) wherein $W^2$ is a suitable leaving group such as, for example, a halogen, in a reaction-inert solvent such as, for example, tetrahydrofuran, diethylether, and in the presence of a suitable base such as, for example, butyl lithium, thus forming an intermediate of formula (VIII). The hydroxy group of the intermediates of formula (VIII) may be eliminated by using a suitable reagent such as for example, formamide in acetic acid or triethylsilane in trifluoroacetic acid, thus obtaining an intermediate of formula (IX) of which the nitro group may subsequently be reduced to an amino group which in turn may then be converted to the 6-azauracil group as described in EP-A-0, 170,316, thus obtaining compounds of formula (I-a-1).

Scheme 1

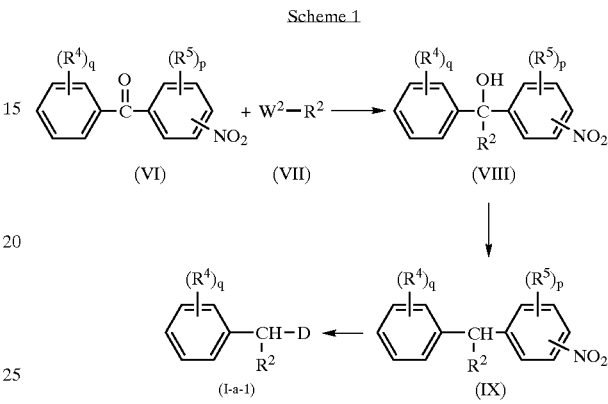

In addition to the reaction procedure shown in scheme 1, other compounds of formula (I) wherein X is a direct bond may be prepared starting from a ketone of formula (X) (Scheme 2). Reacting said ketone of formula (X) with an intermediate of formula (III) wherein X is a direct bond, said intermediates being represented by formula (III-a), results in a compound of formula (I) wherein $R^1$ is hydroxy and X is a direct bond, said compounds being represented by formula (I-a-2). Said reaction may be performed in a reaction-inert solvent such as, for example, tetrahydrofuran, diethylether, diisopropyl-acetamide or a mixture thereof, in the presence of a base such as, for example, butyl lithium. Alternatively, intermediate of formula (III-a) may first be transformed into a Grignard reagent, which may then be reacted with the ketone of formula (X). Said compounds of formula (I-a-2) may further be converted to compounds of formula (I) wherein $R^1$ is a $C_{1-6}$alkyloxy group represented by formula (I-a-3) using art-known group transformation reactions. The compounds of formula (I-a-2) may also be converted to compounds of formula (I) wherein $R^1$ is halo, said compounds being represented by formula (I-a-4). A convenient procedure is converting the hydroxy group to a chlorine atom using a suitable reagent such as, for example, thionyl chloride. Said compounds of formula (I-a4) may further be converted to compounds of formula (I) wherein $R^1$ is amino, said compounds being represented by formula (I-a-5), using ammonia or a functional derivative thereof, in a reaction-inert solvent such as, for example, tetrahydrofuran; or may be converted to compounds of formula (I-a-3) using art-known group transformation reactions.

Reducing the ketone of formula (X) to its corresponding hydroxy derivative of formula (XI) using a suitable reducing agent such as, for example, sodiumborohydride in a reaction-inert solvent such as for example, water, an alcohol, tetrahydrofuran or a mixture thereof; subsequently converting said hydroxy group to a suitable leaving group $W^4$ being for example a halogen, thus obtaining an intermediate of formula (XII), and finally reacting said intermediate of formula (XII) with an intermediate of formula (III) in a suitable solvent such as, for example, tetrahydrofuran, N,N- dimethyl-formamide, acetonitrile, acetic acid, ethanol or a mixture thereof, and optionally in the presence of a suitable base such as, for example, 1,8-diazabicyclo[5.4.0]undec-7-ene or sodiumbicarbonate, will result in a compound of formula (I) wherein $R^1$ is hydrogen, said compounds being represented by formula (I-b).

Alternatively, intermediates of formula (XI) can be directly transformed to compounds of formula (I-b) wherein X is S, said compounds being represented by formula acid or a functional derivative thereof, at elevated temperatures. The resulting intermediate of formula (XII) is hydrolysed to the corresponding amine of formula (XIV), which may then be further reacted with an intermediate of formula (XV) wherein $W^3$ is a suitable leaving group, in the presence of a suitable base, such as, for example pyridine, optionally in the presence of a reaction-inert solvent such as, for example, dichloromethane.

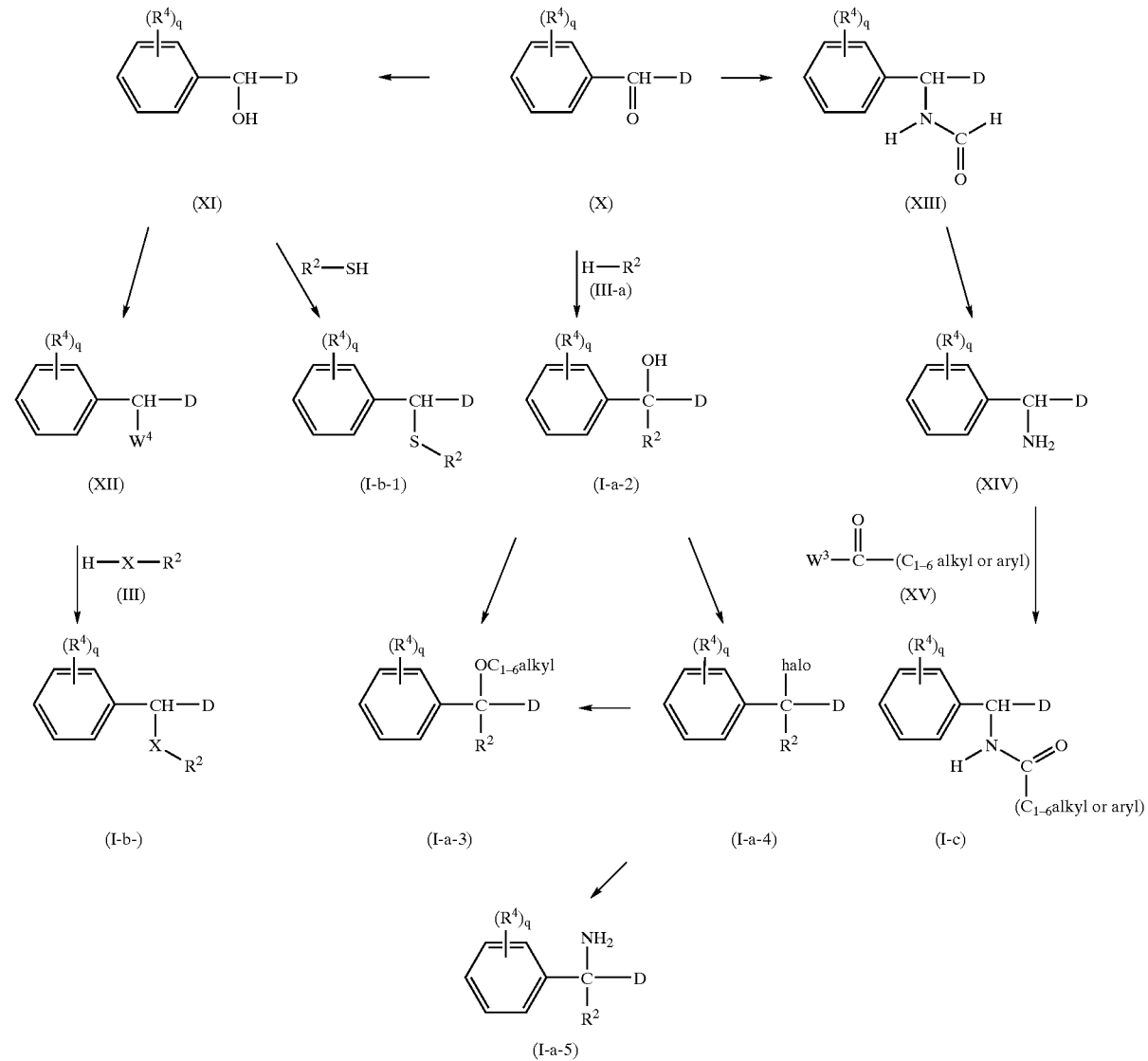

Scheme 2

(I-b-1), using a suitable mercapto containing reagent of formula $R^2$—SH in a suitable reaction solvent such as, for example, trifluoroacetic acid, methanesulfonic acid, trifluoromethanesulfonic acid or the like.

Also starting from a ketone of formula (X), compounds of formula (I) may be prepared wherein $R^1$ is hydrogen and —X—$R^2$ is —NH—C(=O)-(aryl or $C_{1-6}$alkyl), said compounds being represented by formula (I-c). To that effect, a ketone of formula (X) is reacted with formamide in formic Compounds of formula (I) wherein X is a direct bond and $R^2$ is a heterocycle, said compounds being generally represented by formula (I-d), can conveniently be prepared by cyclisation of the appropriate intermediate. Intramolecular cyclisation procedures are feasible and scheme 3 lists several examples.

Starting point is the conversion of the cyano group of a compound of formula (I) wherein —X—$R^2$ is cyano, said compounds being represented by formula (I-e), to a carboxyl group thus forming intermediates of formula (XVII) using art-known techniques such as, for example, using a combi nation of sulphuric and acetic acid in water, which in turn may be further reacted to acyl halides of formula (XVIII), for instance, the acyl chloride derivative may be prepared using thionyl chloride.
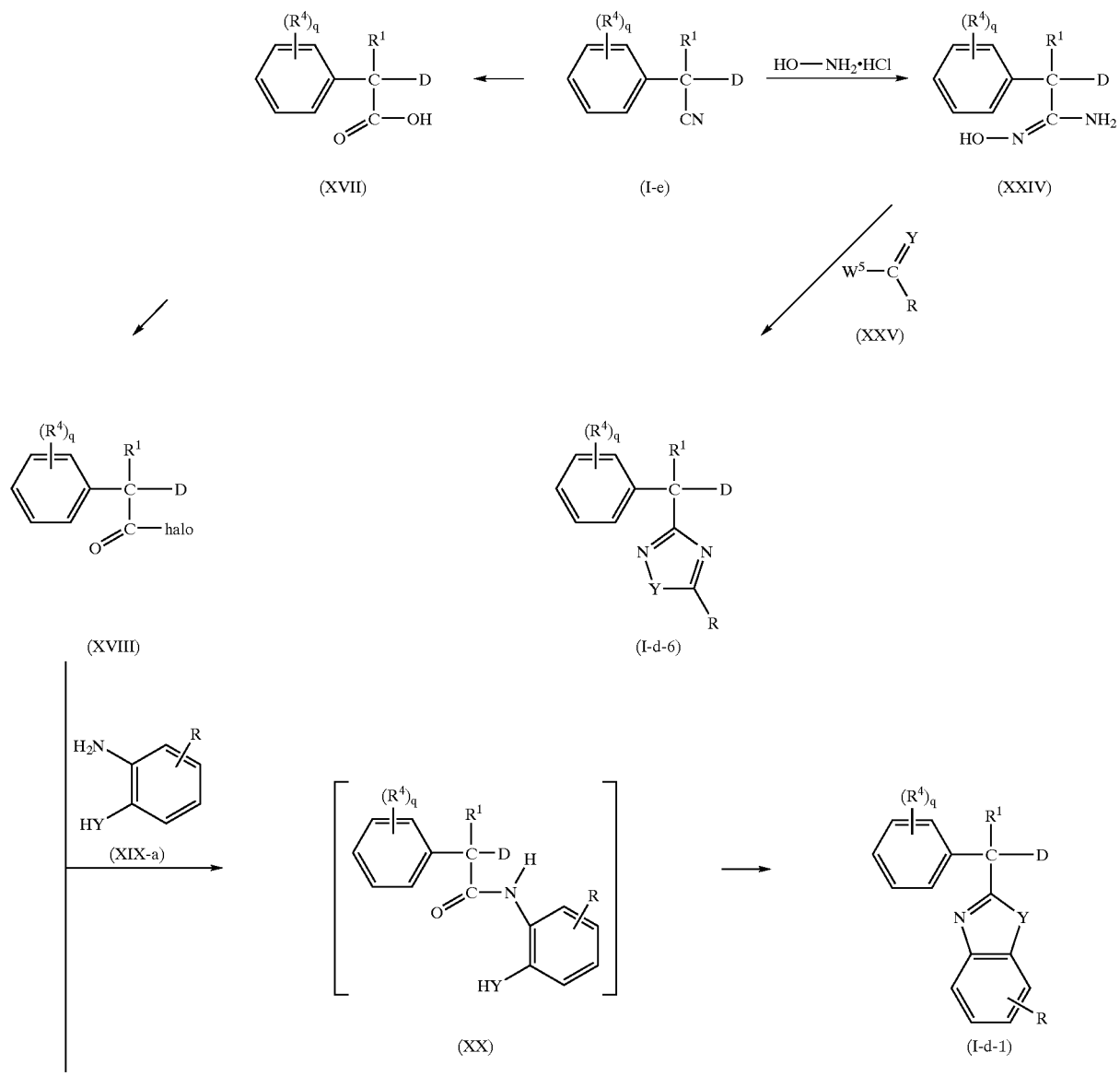

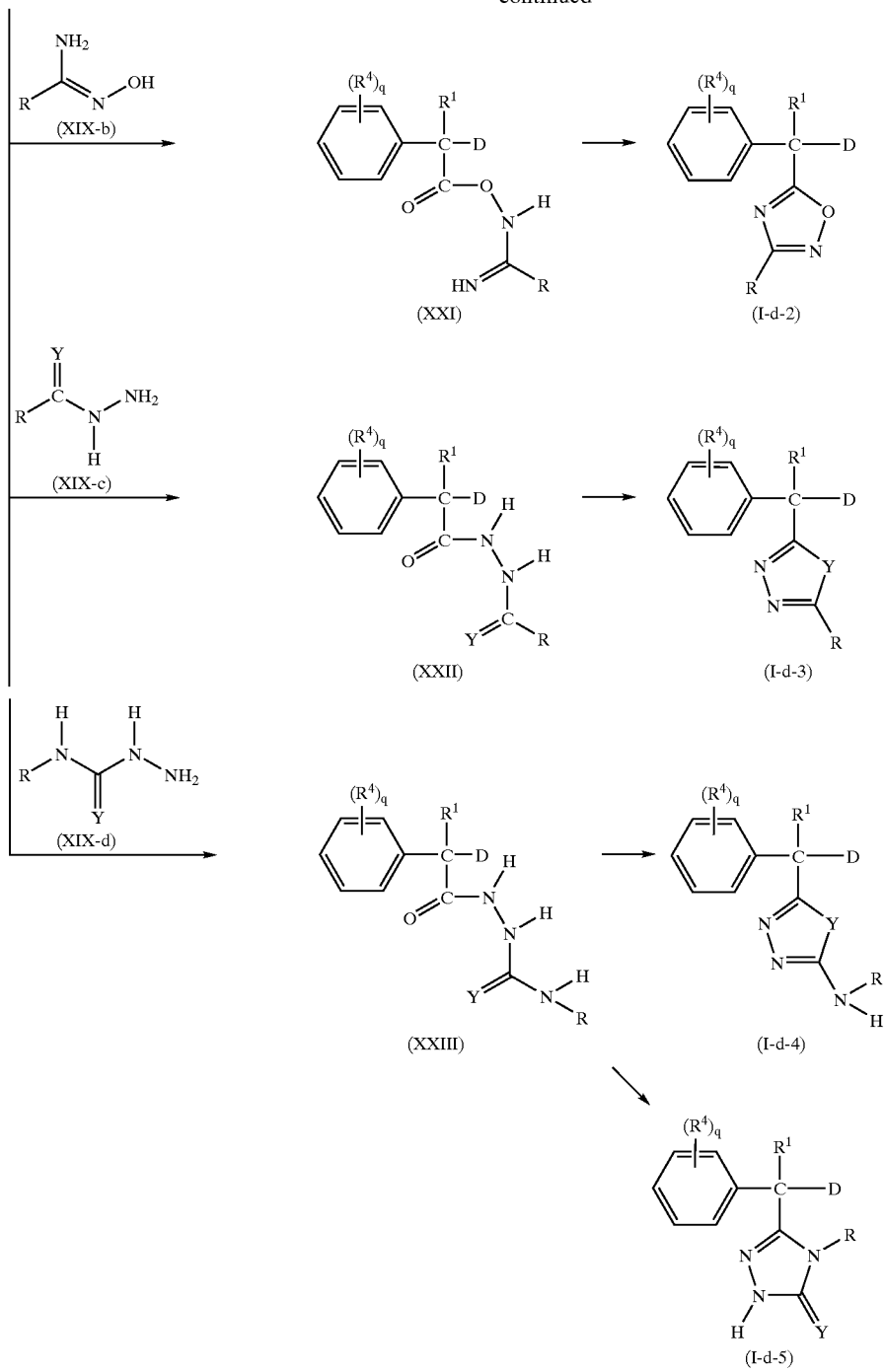

The intermediate of formula (XVIII) may be reacted with an intermediate of formula (XIX-a) wherein Y is O, S or $NR^3$, to form an intermediate of formula (XX) in the presence of a base such as, for example, pyridine. Said intermediate of formula (XX) may further be cyclised to a compound of formula (I) wherein —X—$R^2$ is an optionally substituted benzothiazole or benzoxazole, said compounds being represented by formula (I-d-1), in the presence of a suitable solvent such as, for example, acetic acid, at an elevated temperature, preferably at reflux temperature. It may be convenient to prepare compounds of formula (I-d-1) without isolating intermediates of formula (XX).

Analogously, an intermediate of formula (XVIII) may be reacted with an intermediate of formula (XIX-b) to form an intermediate of formula (XXI) which is cyclised to a compound of formula (I) wherein —X—$R^2$ is an optionally 3-substituted 1,2,4-oxadiazole, said compounds being represented by formula (I-d-2), in a reaction-inert solvent such as, for example, toluene, at an elevated temperature, preferably at reflux temperature. Also analogously, an intermediate of formula (XVI) may be reacted with an intermediate of formula (XIX-c) wherein Y is O, S or $NR^3$, to form an intermediate of formula (XXII) which is cyclised to a compound of formula (I) wherein —X—$R^2$ is an optionally substituted 1,2,4-triazole, 1,3,4-thiadiazole or 1,3,4-oxadiazole, said compounds being represented by formula (I-d-3), in a suitable solvent such as, for example, phosphorus oxychloride.

Also analogously, an intermediate of formula (XVIII) may be reacted with an intermediate of formula (XIX-d) wherein Y is O, S or NR³, to form an intermediate of formula (XXIII) which is cyclised to a compound of formula (I) wherein —X—R² is an optionally amino substituted 1,2,4-triazole, 1,3,4-thiadiazole or 1,3,4-oxadiazole, said compounds being represented by formula (I-d4) in a reaction-inert solvent such as, for example, toluene, and in the presence of an acid; or, which is cyclised to a compound of formula (I) wherein —X—R² is a disubstituted 1,3,4-triazole, said compounds being represented by formula (I-d-5).

The nitrile derivative of formula (XVI) may also be reacted with hydroxylamine hydrochloride or a functional derivative thereof, thus forming an intermediate of formula (XXIV) which may be reacted with an intermediate of formula (XXV) to form a compound of formula (I) wherein —X—R² is an optionally 5-substituted 1,2,4-triazole, 1,2,4-thiadiazole or 1,2,4-oxadiazole, said compounds being represented by formula (I-d-6), in a reaction-inert solvent such as, for example, methanol, butanol or a mixture thereof, and in the presence of a base such as, for example, sodium methanolate.

Compounds of formula (I-d) wherein the heterocycle is substituted 2-thiazolyl, said compounds being represented by formula (I-d-7), can be prepared by reacting an intermediate of formula (XVI) with hydrogensulfide or a functional derivative thereof, in a reaction inert solvent such as, for example, pyridine, optionally in the presence of a suitable base such as, for example, triethylamine, thus forming an intermediate of formula (XXVI), which may subsequently be reacted with an intermediate of formula (XXVII) or a functional derivative thereof such as the ketal derivative thereof, in a reaction-inert solvent such as for example, ethanol, and optionally in the presence of an acid such as, for example, hydrogenchloride.

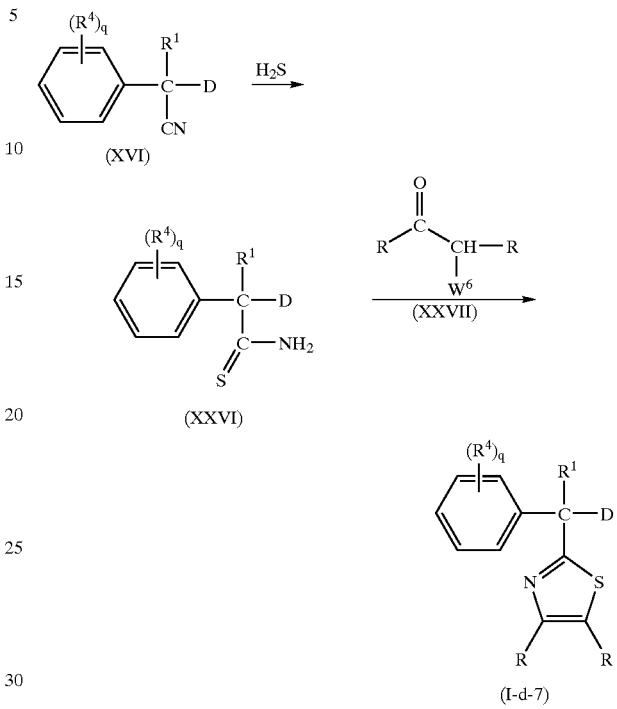

Compounds of formula (I-d) wherein the heterocycle is substituted 5-thiazolyl and R¹ is hydrogen, said compounds being represented by formula (I-d-8), can be prepared following the reaction procedure depicted in scheme 4.

Scheme 4

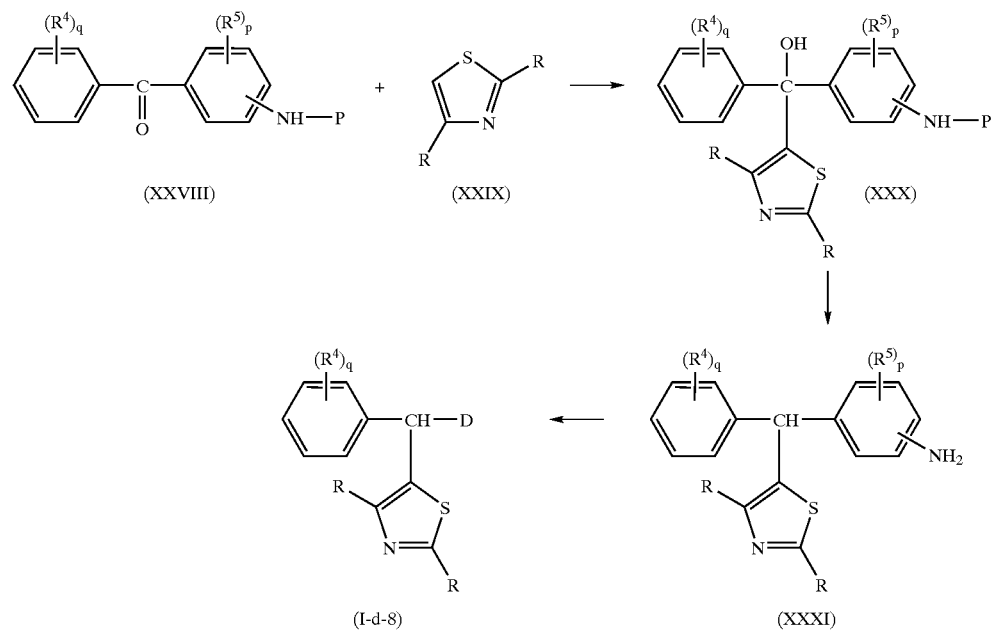

Initially, an intermediate of formula (XXVIII) wherein P is a protective group such as, for example, a $C_{1-6}$alkylcarbonyl group, is reacted with a thiazole derivative of formula (XXIX) in the presence of a suitable base such as, for example, butyl lithium, in a reaction inert solvent such as, for example, tetrahydrofuran, thus forming an intermediate of formula (XXX). It may be convenient to perform said reaction under an inert atmosphere at lower temperature, preferably at about –70° C. The hydroxy group and the protective group P of said intermediates (XXX) may be removed using art-known procedures such as, for example, stannous chloride and hydrochloric acid in acetic acid, thus forming an intermediate of formula (XXXI), of which the amino group may further be converted to a 6-azauracil moiety according to the procedure described in EP-A-0,170,316, thus forming a compound of formula (I-d-8).

Also, compounds of formula (I-d) wherein the heterocycle is 4-thiazolyl, said compounds being represented by formula (I-d-9), can be prepared following the reaction procedure depicted in scheme 5.

ate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g. counter-current distribution, liquid chromatography and the like.

Some of the compounds of formula (I) and some of the intermediates in the present invention may contain an asym- Scheme 5

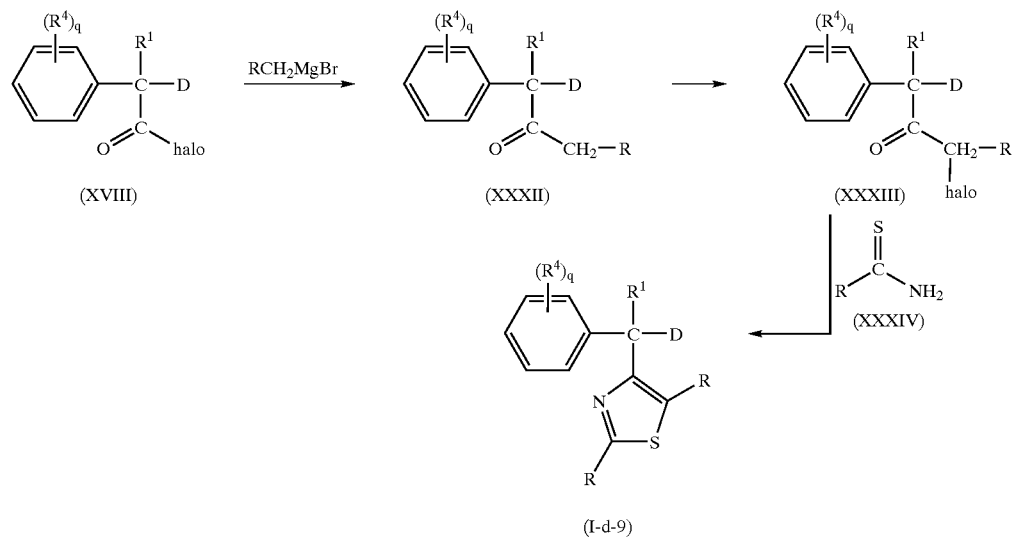

An intermediate of formula (XVIII) is reacted with a Grignard reagent of formula $RCH_2MgBr$ or a functional derivative thereof to form an intermediate of formula (XXXII), which may be halogenated, preferably brominated, in the a-position using a suitable reagent such as trimethylphenylammonium tribromide in tetrahydrofuran, thus forming an intermediate of formula (XXXII). Said intermediate (XXXI) may then be reacted with a thioamide of formula (XXXIV) to form a compound of formula (I-d9), in a reaction-inert solvent such as, for example, ethanol, at an elevated temperature, preferably reflux temperature.

The compounds of formula (I) can also be converted into each other following art-known procedures of functional group transformation of which some examples are. mentioned hereinabove.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an approprimetric carbon atom. Pure stereochemically isomeric forms of said compounds and said intermediates can be obtained by the application of art-known procedures. For example, diastereoisomers can be separated by physical methods such as selective crystallisation or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallisation or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials as used in the reaction procedures mentioned hereinabove are known compounds and may be commercially available or may be prepared according to art-known procedures.

IL-5, also known as eosinophil differentiating factor (EDF) or eosinophil colony stimulating factor (Eo-CSF), is a major survival and differentiation factor for eosinophils and therefore thought to be a key player in eosinophil infiltration into tissues. There is ample evidence that eosinophil influx is an important pathogenic event in bronchial asthma and allergic diseases such as, cheilitis, irritable bowel disease, eczema, urticaria, vasculitis, vulvitis, winterfeet, atopic dermatitis, pollinosis, allergic rhinitis and allergic conjunctivitis; and other inflammatory diseases, such as eosinophilic syndrome, allergic angiitis, eosinophilic fasciitis, eosinophilic pneumonia, PIE syndrome, idiopathic eosinophilia, eosinophilic myalgia, Crohn's disease, ulcerative colitis and the like diseases.

The present compounds also inhibit the production of other chemokines such as monocyte chemotactic protein-1 and -3 (MCP-1 and MCP-3). MCP-1 is known to attract both T-cells, in which IL-5 production mainly occurs, and monocytes, which are known to act synergetically with eosinophils (Carr et al., 1994, Immunology, 91, 3652–3656). MCP-3 also plays a primary role in allergic inflammation as it is known to mobilize and activate basophil and eosinophil leukocytes (Baggiolini et al., 1994, Immunology Today, 15(3), 127–133).

The present compounds have no or little effect on the production of other chemokines such as IL-1, IL-2, IL-3, IL-4, IL-6, IL-10, γ-interferon (IFN-γ) and granulocyte-macrophage colony stimulating factor (GM-CSF) indicating that the present IL-5 inhibitors do not act as broad-spectrum immunosuppressives.

The selective chemokine inhibitory effect of the present compounds can be demonstrated by in vitro chemokine measurements in human blood. In vivo observations such as the inhibition of eosinophilia in mouse ear, the inhibition of blood eosinophilia in the Ascaris mouse model; the reduction of serum IL-5 protein production and splenic IL-5 mRNA expression induced by anti-CD3 antibody in mice and the inhibition of allergen- or Sephadex-induced pulmonary influx of eosinophils in guinea-pig are indicative for the usefulness of the present compounds in the treatment of eosinophil-dependent inflammatory diseases.

The present inhibitors of IL-5 production are particularly useful for administration via inhalation.

The intermediates of formula (XI-a) are interesting intermediates. Not only have they a particular usefulness as intermediates in the preparation of the compounds of formula (I), they also have valuable pharmacological activity.

In view of the above pharmacological properties, the compounds of formula (I) can be used as a medicine. In particular, the present compounds can be used in the manufacture of a medicament for treating eosinophil-dependent inflammatory diseases as mentioned hereinabove, more in particular bronchial asthma, atopic dertmatitis, allergic rhinitis and allergic conjunctivitis.

In view of the utility of the compounds of formula (I), there is provided a method of treating warm-blooded animals, including humans, suffering from eosinophil-dependent inflammatory diseases, in particular bronchial asthma, atopic dertmatitis, allergic rhinitis and allergic conjunctivitis. Said method comprises the systemic or topical administration of an effective amount of a compound of formula (I), a N-oxide form, a pharmaceutically acceptable addition salt or a possible stereoisomeric form thereof, to warm-blooded animals, including humans.

The present invention also provides compositions for treating eosinophil-dependent inflammatory diseases comprising a therapeutically effective amount of a compound of formula (I) and a pharmaceutically acceptable carrier or diluent.

To prepare the pharmaceutical compositions of this invention, a therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as parenteral administration; or topical administration such as via inhalation, a nose spray or the like. Application of said compositions may be by aerosol, e.g. with a propellant such as nitrogen, carbon dioxide, a freon, or without a propellant such as a pump spray, drops, lotions, or a semisolid such as a thickened composition which can be applied by a swab. In particular, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In order to enhance the solubility and/or the stability of the compounds of formula (I) in pharmaceutical compositions, it can be advantageous to employ α-, β- or γ-cyclo-dextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxypropyl or hydroxybutyl; carboxy$C_{1-6}$alkyl, particularly carboxymethyl or carboxy-ethyl; $C_{1-6}$alkylcarbonyl, particularly acetyl; $C_{1-6}$alkyloxycarbonyl$C_{1-6}$alkyl or carboxy-$C_{1-6}$alkyloxy$C_{1-6}$alkyl, particularly carboxymethoxypropyl or carboxyethoxy-propyl; $C_{1-6}$alkylcarbonyloxy$C_{1-6}$alkyl, particularly 2-acetyloxypropyl. Especially noteworthy as complexants and/or solubilizers are β-CD, randomly methylated β-CD, 2,6-dimethyl-γ-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The M.S. value can be determined by various analytical techniques, preferably, as measured by mass spectrometry, the M.S. ranges from 0.125 to 10.

The average substitution degree (D.S.) refers to the average number of substituted hydroxyls per anhydroglucose unit. The D.S. value can be determined by various analytical techniques, preferably, as measured by mass spectrometry, the D.S. ranges from 0.125 to 3.

Due to their high degree of selectivity as IL-5 inhibitors, the compounds of formula (I) as defined above, are also useful to mark or identify receptors. To this purpose, the compounds of the present invention need to be labelled, in particular by replacing, partially or completely, one or more atoms in the molecule by their radioactive isotopes. Examples of interesting labelled compounds are those compounds having at least one halo which is a radioactive isotope of iodine, bromine or fluorine; or those compounds having at least one $^{11}$C-atom or tritium atom.

One particular group consists of those compounds of formula (I) wherein $R^4$ and/or $R^5$ are a radioactive halogen atom. In principle, any compound of formula (I) containing a halogen atom is prone for radiolabelling by replacing the halogen atom by a suitable isotope. Suitable halogen radioisotopes to this purpose are radioactive iodides, e.g. $122_I$, $123_I$, $125_I$, $131_I$; radioactive bromides, e.g. $^{75}$Br, $^{76}$Br, $^{77}$Br and $^{82}$Br, and radioactive fluorides, e.g. $^{18}$F. The introduction of a radioactive halogen atom can be performed by a suitable exchange reaction or by using any one of the procedures as described hereinabove to prepare halogen derivatives of formula (I).

Another interesting form of radiolabelling is by substituting a carbon atom by a $^{11}$C-atom or the substitution of a hydrogen atom by a tritium atom.

Hence, said radiolabelled compounds of formula (I) can be used in a process of specifically marking receptor sites in biological material. Said process comprises the steps of (a) radiolabelling a compound of formula (I), (b) administering this radio-labelled compound to biological material and subsequently (c) detecting the emissions from the radiolabelled compound. The term biological material is meant to comprise every kind of material which has a biological origin. More in particular this term refers to tissue samples, plasma or body fluids but also to animals, specially warm-blooded animals, or parts of animals such as organs.

The radiolabelled compounds of formula (I) are also useful as agents for screening whether a test compound has the ability to occupy or bind to a particular receptor site. The degree to which a test compound will displace a compound of formula (I) from such a particular receptor site will show the test compound ability as either an agonist, an antagonist or a mixed agonist/antagonist of said receptor.

When used in in vivo assays, the radiolabelled compounds are administered in an appropriate composition to an animal and the location of said radiolabelled compounds is detected using imaging techniques, such as, for instance, Single Photon Emission Computerized Tomography (SPECT) or Positron Emission Tomography (PET) and the like. In this manner the distribution of the particular receptor sites throughout the body can be detected and organs containing said receptor sites can be visualised by the imaging techniques mentioned hereinabove. This process of imaging an organ by administering a radiolabelled compound of formula (I) and detecting the emissions from the radioactive compound also constitutes a part of the present invention.

In general, it is contemplated that a therapeutically effective daily amount would be from 0.01 mg/kg to 50 mg/kg body weight, in particular from 0.05 mg/kg to 10 mg/kg body weight. A method of treatment may also include administering the active ingredient on a regimen of between two or four intakes per day.

EXPERIMENTAL PART

A. Preparation of Compounds of Formula (I)

Example A1

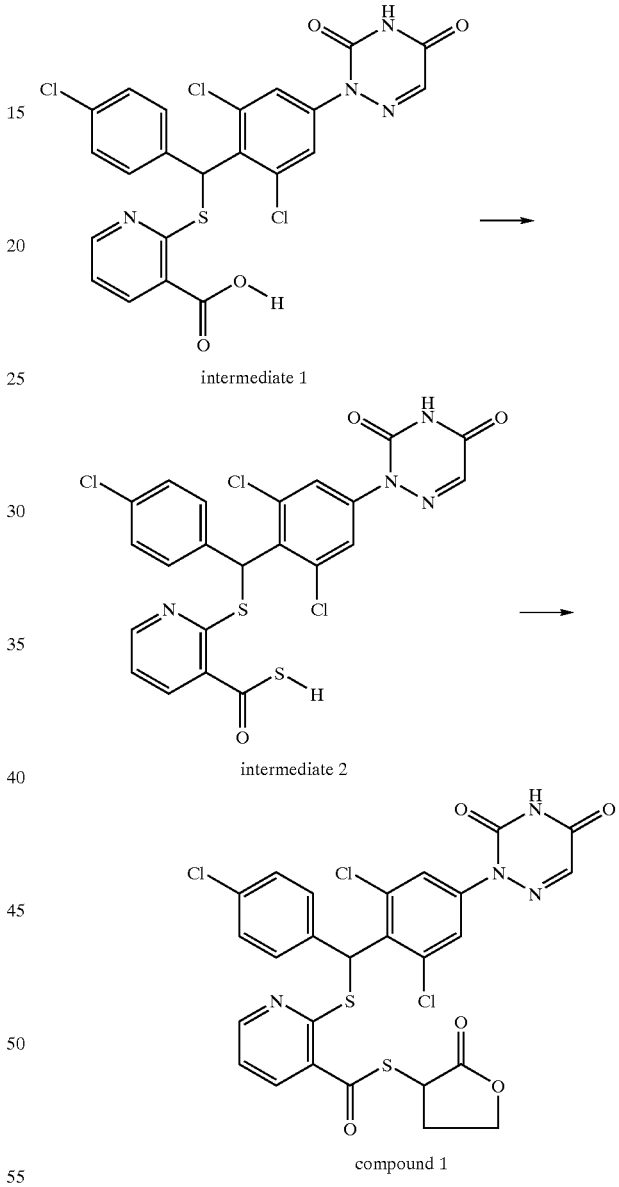

intermediate 1 intermediate 2 compound 1 a) A mixture of 2-[3,5-dichloro-4-[(4-chlorophenyl)hydroxymethyl]phenyl-1,2,4-triazine-3,5(2H,4H)-dione (0.0063 mol) and 1,2-dihydro-2-thioxo-3-pyridinecarboxylic acid (0.0063 mol) was added portionwise to methanesulfonic acid (20 ml), stirred at room temperature for 2 hours. The reaction mixture was poured out into ice-water and ethylacetate was added. The organic layer was separated, washed with brine, dried, filtered and the solvent was evaporated. The residue was stirred in boiling ethanol, filtered off, washed with diisopropyl ether and dried, yielding 3.1 g (91%) of intermediate (1) {MS (ES+) m/z 535 [MH⁺]}.

b) Reaction under $N_2$ atmosphere. A solution of intermediate (1) (0.00187 mol) in N,N-dimethylformamide (20 ml) was treated with 1,1'-carbonylbis-1H-imidazole (0.00373 mol) and the mixture was stirred for 12 hours at room temperature. $H_2S$ was bubbled through the mixture for 15 to 30 minutes. Then, the reaction mixture was stirred for 2 hours. The mixture was poured out into ice-water (brine) and extracted 3 times with ethylacetate. The combined organic layers were washed with brine, dried, filtered and the solvent was evaporated. The residue was co-evaporated 3 times with toluene, yielding 1 g (100%) of intermediate (2) {MS (ES+) m/z 551 [MH⁺]}.

c) A solution of 3-bromodihydro-2(3H)-furanone (1 mmol) in N,N-dimethylformamide (2 ml) was added dropwise to an ice-cold suspension of intermediate 2 (0.91 mmol) and $NaHCO_3$ (1 mmol) in N,N-dimethylformamide (5 ml). The reaction mixture was stirred for 15 minutes, and then partitioned between water (25 ml) and ethylacetate (25 ml). The organic layer was separated, washed with water (2×25 ml), dried, filtered and the solvent was evaporated. The residue was purified by silicagel chromatography (eluent: ethyl acetate/hexane, gradient from 20–80 to 80–20% (v/v)). The pure fractions were collected and their solvent evaporated, yielding 0,243 g (42%) of compound (1) {MS (ES+) m/z 635 [MH⁺]}.

Example A2

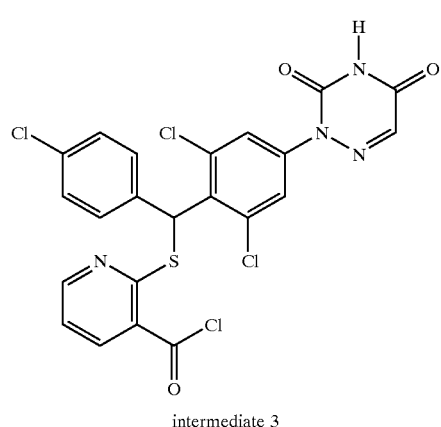

intermediate 3

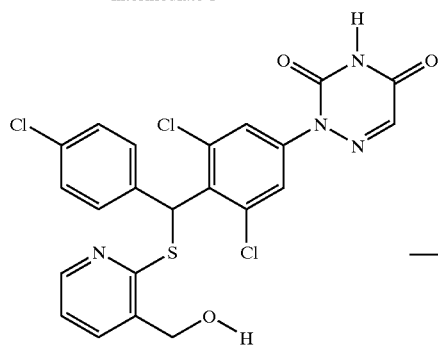

intermediate 4

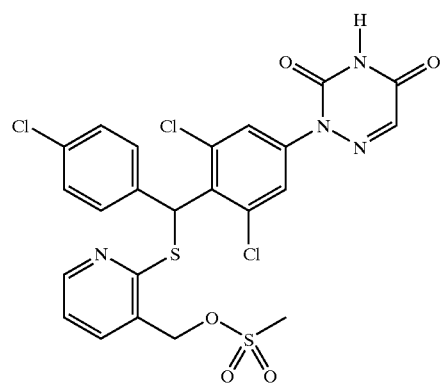

intermediate 5

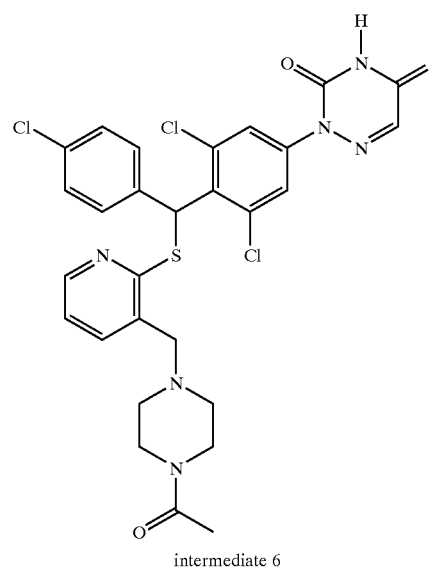

intermediate 6

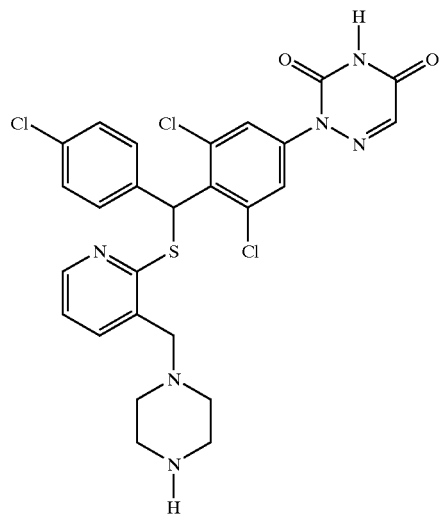

intermediate 7

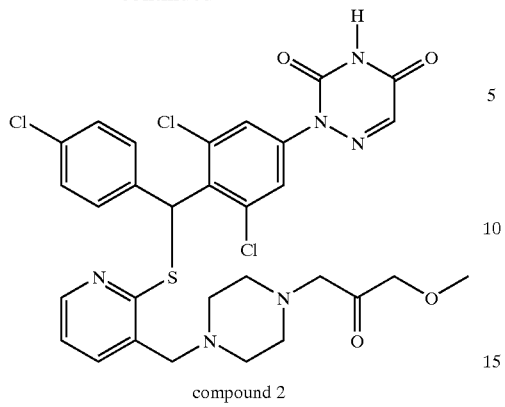

compound 2 a) A mixture of intermediate 1 (0.075 mol) in SOCl$_2$ (300 ml) was stirred and refluxed for 2 hours. The solvent was evaporated. The residue was dissolved in toluene and the solvent was evaporated, yielding 41.6 g of intermediate 3.

b) NaBH$_4$ (0.495 mol) was added portionwise over 90 min to a mixture of intermediate 3 (0.075 mol) in 1,4-dioxane (500 ml), stirred at room temperature. The resulting mixture was stirred for 48 hours at room temperature, then cooled on an ice-bath. HCl (2 N) was added dropwise (until pH=2) and this mixture was extracted with CH$_2$Cl$_2$. The separated organic layer was dried, filtered and the solvent evaporated. The residue was purified over silica gel on a glass filter (eluent: CH$_2$Cl$_2$/CH$_3$OH 97/3). The pure fractions were collected and the solvent was evaporated, yielding 2.2 g of intermediate 4.

c) A mixture of intermediate 4 (0.004 mol) and triethylamine (0.005 mol) in CH$_2$Cl$_2$ (40 ml) was stirred at 0–5° C. A solution of methylsulfonylchloride (0.005 mol) in CH$_2$Cl$_2$ (10 ml) was added dropwise over 15 min at 0–5° C. and the resulting reaction mixture was stirred for one hour at ±5° C. Triethylamine (0.70 ml) was added and the resulting reaction mixture was stirred for one hour at 0° C., yielding 2.4 g of intermediate 5.

d) A solution of 1-acetyl-piperazine (0.03624 mol) in CH$_2$Cl$_2$ (30 ml) was added dropwise to a solution of intermediate 5 (0.01208 mol) and triethylamine (0.0302 mol) in CH$_2$Cl$_2$ (150 ml), stirred at 0° C. The reaction mixture was stirred overnight at room temperature, then washed with a saturated NaHCO$_3$ solution, with brine, dried, filtered and the solvent was evaporated. The residue was purified by column chromatography over silica gel (eluent: CH$_2$Cl$_2$/CH$_3$OH gradient from 98/2 to 95/5). The pure fractions were collected and the solvent was evaporated, then co-evaporated ethylacetate. The residue was stirred in 2-methoxy-2-methylpropane, filtered off and dried, yielding 1.51 g (20%) of intermediate 6.

e) Intermediate 6 (0.00321 mol) was dissolved in 1,4-dioxane (50 ml). HCl 2N (0.05 mol) was added and the reaction mixture was stirred and refluxed for 12 hours. The reaction mixture was cooled, poured out slowly into asaturated aqueous NaHCO$_3$ solution (150 ml)+ice (100 g) and this mixture was extracted with CH$_2$Cl$_2$/CH$_3$OH (90/10). The combined organic layers were washed with brine, dried, filtered and the solvent evaporated, then co-evaporated with ethylacetate. When adding ethylacetate for the second time, precipitation resulted. This precipitate was filtered off, washed with diisopropyl ether and dried, yielding 1.39 g (74%) of intermediate 7.

f) A mixture of intermediate 7 (0.0034 mol) in CH$_3$CN (60 ml) was stirred at room temperature. Triethylamine (1.47 ml) was added. Bromoacetic acid, ethyl ester (0.0034 mol) was added dropwise and the resulting reaction mixture was stirred for 90 min at room temperature. The solvent was evaporated. The residue was taken up into CH$_2$Cl$_2$. The organic solution was washed with water. The water layer was extracted with CH$_2$Cl$_2$/CH$_3$OH 90/10. 2) The organic layer was washed with water, combined with the other organic layer, dried, filtered and the solvent was evaporated. The was purified by flash column chromatography, over silica gel (eluent: CH$_2$Cl$_2$/CH$_3$OH 99/1). The pure fractions were collected and the solvent was evaporated. The residue was co-evaporated with ethylacetate. The residue was stirred in diisopropylether, filtered off, washed and dried, yielding 0.44 g of compound 2.

Example A3

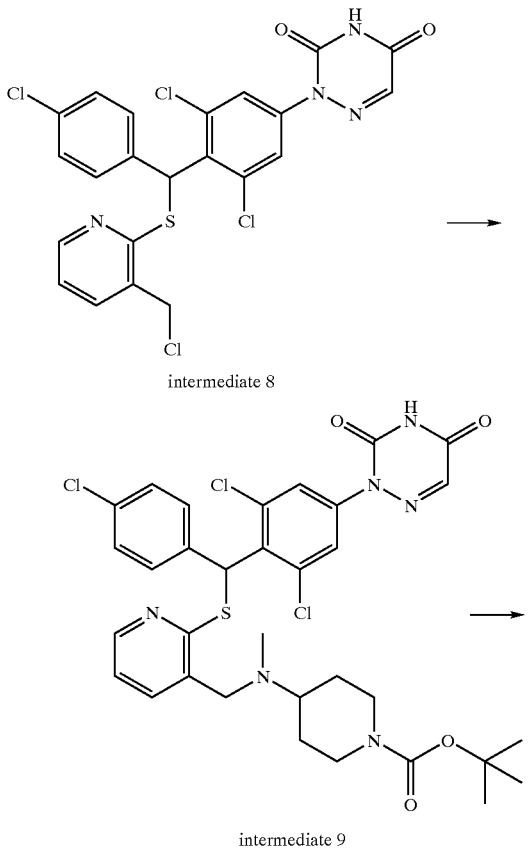

intermediate 8 intermediate 9

-continued

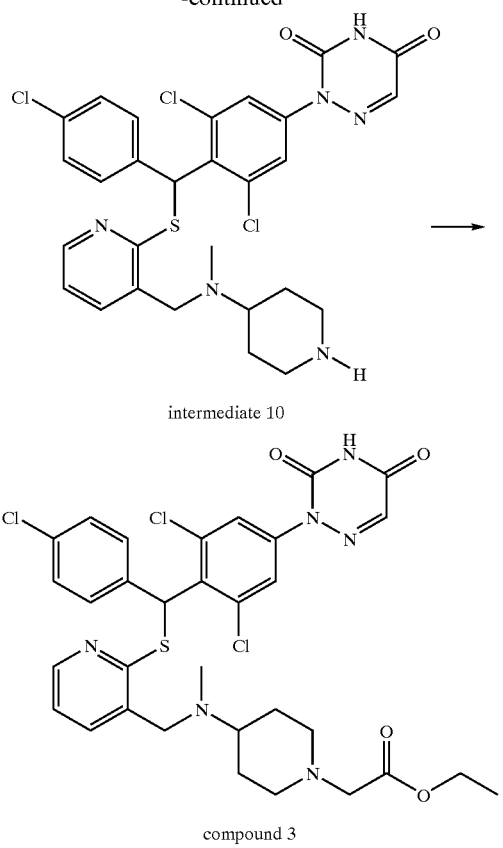

intermediate 10 compound 3 a) CH$_2$Cl$_2$ (20 ml) was stirred at room temperature. HCl (gas) was bubbled through the solution for 15 min. This solution was added dropwise to a solution of intermediate 4 (0.01 mol) in CH$_2$Cl$_2$ (50 ml). The HCl salt precipitated. SOCl$_2$ (0.05 mol) was added and the mixture was stirred and refluxed for 2 hours. SOCl$_2$ (3.6 ml) was added and the reaction mixture was stirred and refluxed for 2 hours. The mixture was cooled. The precipitate was filtered off. Solid and filtrate were recombined. The solvent was evaporated. More CH$_2$Cl$_2$ (70 ml) and SOCl$_2$ (3.6 ml) were added and the reaction mixture was stirred and refluxed for 3 hours, then cooled and the resulting precipitate was filtered off, washed with diisopropylether and dried, yielding 4 g of intermediate 8.

b) A solution of 4-methylamino-1-piperidinecarboxylic acid, 1,1-dimetheylethylester (0.02244 mol) in CH$_3$CN (20 ml) was added to a solution of intermediate 8 (0.00748 mol) in CH$_3$CN (60 ml) and the resulting reaction mixture was for 3 hours at 60° C., then overnight at room temperature. The solvent was evaporated. The residue was stirred in boiling ethylacetate, then filtered off and taken up into CH$_2$Cl$_2$/CH$_3$OH 95/5. The organic solution was washed with brine, dried, filtered and the solvent evaporated. The residue was purified by HPLC over silica (eluent: CH$_2$C$_2$/(CH$_2$Cl$_2$/CH$_3$OH 90/10)/CH$_3$OH (0 min) 100/0/0, (34 min) 65/35/0, (40 min) 50/0/50, (43 min) 0/0/100, (46.6-60 min) 100/0/0). The pure fractions were collected and the solvent was evaporated. The residue was stirred in diisopropylether, filtered off and dried, yielding 3.42 g (64%) of intermediate 9.

c) A mixture of intermediate 9 (0.00409 mol) in methanol (30 ml) and HCl/2-propanol (4 ml) was stirred overnight at room temperature. More HCl/2-propanol (2 ml) was added and stirring was continued for 2 hours. The reaction mixture was poured out into water (300 ml) and CH$_2$Cl$_2$/CH$_3$OH 90/10 (400 ml) was added. The reaction mixture was neutralized by dropwise addition of a saturated aqueous NaHCO$_3$ solution. The layers were separated. The water layer was extracted with CH$_2$Cl$_2$/CH$_3$OH 90/10. The combined organic layers c were dried, filtered and the solvent was evaporated. Ethylacetate was added and azeotroped on the rotary evaporator. The residue stirred in boiling CH$_3$CN, cooled, filtered off, washed with diisopropylether and dried, yielding 2.27 g (90%) intermediate 10.

d) Triethylamine (1.42 ml) was added to intermediate 10 (0.00304 mol) in dimethyl-sulfoxide (100 ml). The mixture stirred at 60° C. Then, bromo acetic acid, ethyl ester (0.00304 mol) was added and the resulting solution was allowed to cool to room temperature, and stirred overnight. The reaction mixture was poured out into water (300 ml) and this mixture was extracted with toluene. The toluene layers were combined, dried, filtered and the solvent was evaporated. The residue was purified by HPLC over silica gel (eluent: CH$_2$Cl$_2$/CH$_3$OH gradient). Two pure-fraction groups were collected and their solvent was evaporated. The desired fraction was dissolved in ethylacetate, filtered through pleated paper filter and the solvent was evaporated. The residue was stirred in n-hexane, filtered off and dried, yielding 0.87 g (41%) of compound 3.

Example A4

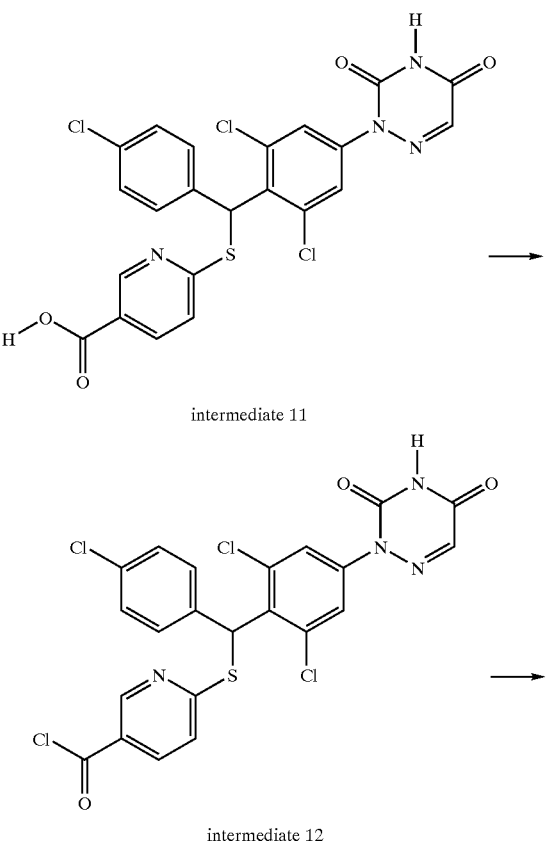

intermediate 11 intermediate 12

-continued

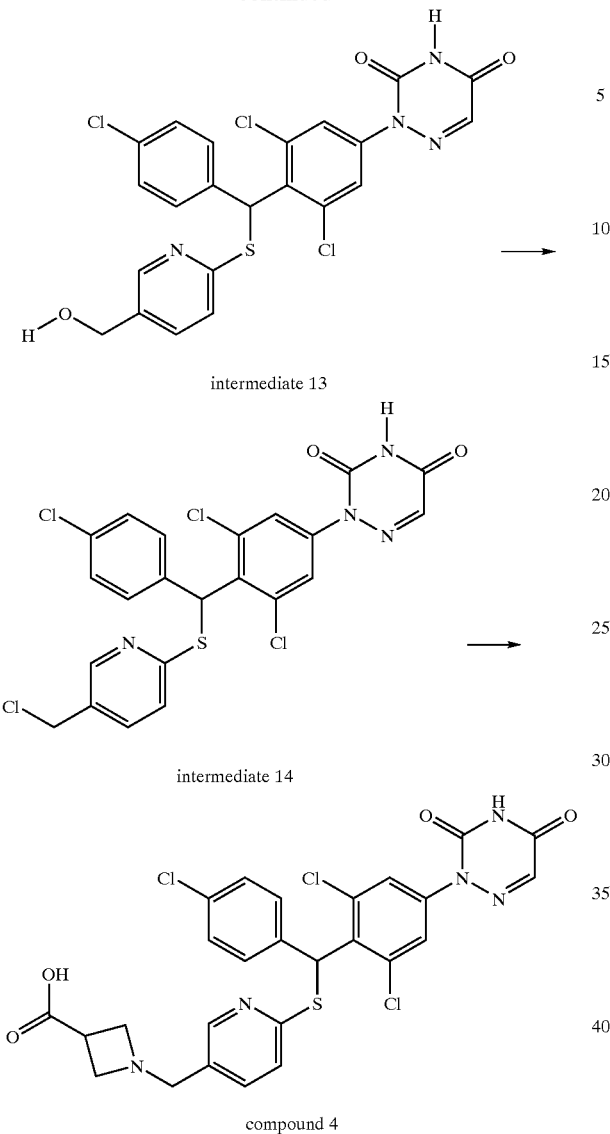

intermediate 13 intermediate 14 compound 4 a) A mixture of 2-[3,5-dichloro4-[(4-chlorophenyl)hydroxymethyl]phenyl]-1,2,4-triazine-3,5(2H,4H)-dione (0:05 mol) [CAS 219981-46-1] and 6-mercapto-3-piperidinecarboxylic acid (0.05 mol) was added portionwise over 1 hour to methane-sulfonic acid (100 ml), stirred at room temperature. The reaction was stirred overnight at room temperature, then poured out into ice-water and this mixture was extracted with ethylacetate. The organic layer was separated, dried, filtered and the solvent was evaporated, yielding 26.8 g of intermediate 11.

b) A mixture of intermediate 11 (0.05 mol) in $SOCl_2$ (250 ml) was stirred and refluxed for 2 hours. The solvent was evaporated. The residue was dissolved in toluene and the solvent was evaporated, yielding 27.7 g of intermediate 12.

c) $NaBH_4$ (0.33 mol) was added portionwise over 60 min to a mixture of intermediate 12 (0.05 mol) in 1,4-dioxane (350 ml), stirred at room temperature. The resulting reaction mixture was stirred for 2 hours at room temperature, then cooled on an ice-bath. HCl (conc.) was added dropwise until acidic. Water was added and this mixture was extracted with $CH_2Cl_2$. The separated organic layer was dried, filtered and the solvent evaporated. The residue was purified over silica gel on a glass filter (eluent: $CH_2Cl_2/CH_3OH$ from 98/2 to 97/3). The pure fractions were collected and the solvent was evaporated, yielding 10.4 g intermediate 13.

d) A mixture of $SOCl_2$ (0.2375 mol) in $CH_2Cl_2$ (200 ml) was stirred at room temperature. A mixture of intermediate 13 (0.0475 mol) in $CH_2Cl_2$ (50 ml) was added dropwise. The reaction mixture was stirred for 2 hours at room temperature. The solvent was evaporated. The residue was stirred in diisopropylether, filtered off and dried, yielding 23.8 g intermediate 14.

e) Triethylamine (0.001388 mol) was added to a solution of intermediate 14 (0.000347 mol) and 3-azetidinylcarboxylic acid (0.000381 mol) in $CH_3CN$ (4 ml). The reaction mixture was stirred for 12 hours at 60° C. The desired compound was isolated and purified by HPLC (eluent gradient: $CH_3CN/H_2O$). The desired fractions were collected and the solvent was evaporated, yield 0.009 g (5%) of compound 4.

Example A5 compound 5

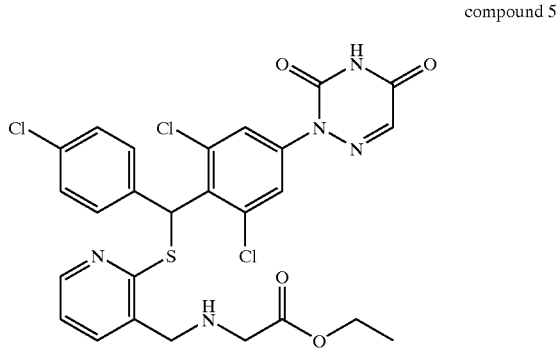

A mixture of intermediate 5 (0.004 mol), glycine, ethyl ester hydrochloride (0.0044 mol) and triethylamine (0.016 mol) in $CH_3CN$ (50 ml) was stirred for 24 hours at 50° C. The solvent was evaporated. The residue was stirred in water and extracted with $CH_2Cl_2$. The separated organic layer was dried, filtered and the solvent evaporated. The residue was purified by flash column chromatography over silica gel (eluent: $CH_2Cl_2/CH_3OH$ from 99.5/0.5 to 98/2). The desired fractions were collected and the solvent was evaporated. The residue was further purified by HPLC (eluent: (0.5% $NH_4OAc$ in $H_2O)/CH_3CN/CH_3OH$ gradient). The pure fractions were collected and the solvent was evaporated. The residue was dried, yielding 0.11 g (4.5%) of compound 5.

Example A6

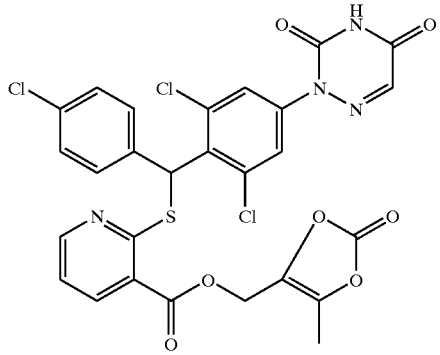

compound 6

A solution of 4-(bromomethyl)-5-methyl-1,3-dioxol-2-one (0.0062 mol) in N,N-dimethylformamide (5ml) was added dropwise to a solution of intermediate 1 (0.00373 mol) and 1H-imidazole (0.007 mol) in in N,N-dimethylformamide (25 ml). The mixture was stirred at 60° C. overnight. The solvent was evaporated in. The residue was taken up in ethylacetate, washed with H₂O and a saturated NaCl solution. The organic layer was separated, dried, filtered and the solvent was evaporated. The residue was purified by column chromatography over silicagel (eluent: hexane/ethylacetate 75/25). The desired fractions were collected and the solvent was evaporated. The residue was purified again over silica gel on a glass filter (eluent: hexane/ethylacetate 75/25 to 50/50). The pure fractions were collected and the solvent was evaporated. The residue was stirred in diisopropylether. The precipitate was filtered off, washed with diisopropylether and dried, yielding 0.595g (25%) of compound 6.

What is claimed is:

1. A compound selected from the group consisting of:

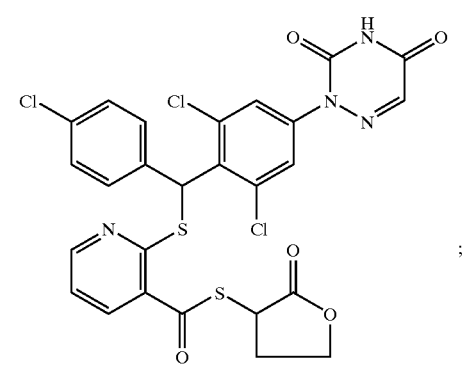

;

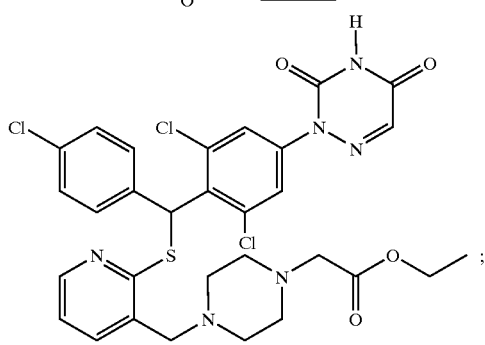

;

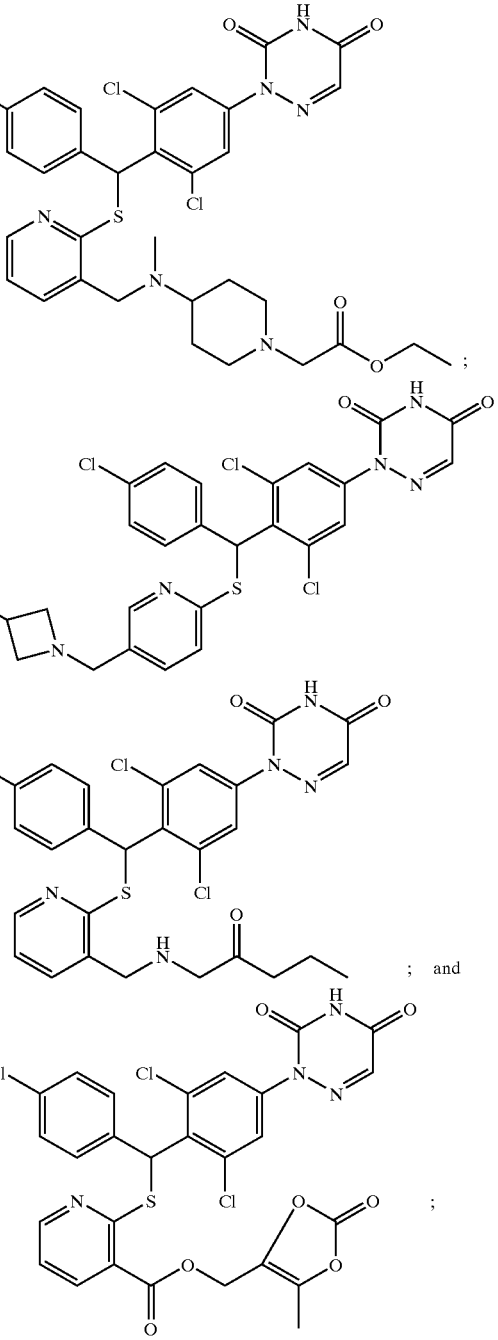

and an N-oxide, a pharmaceutically acceptable addition salt, or a stereochemically isomeric form thereof.

2. A composition comprising a pharmaceutically acceptable carrier and, as active ingredient, a therapeutically effective amount of a compound as claimed in claim 1.

3. A method for treating bronchial asthma in a patient, comprising administering a compound according to claim 1 to said patient.

4. A process of marking a receptor comprising the steps of
a) radiolabelling a compound as defined in claim 1;
b) administering said radiolabelled compound to biological material, and
c) detecting the emissions from the radiolabelled compound.

5. A process of imaging an organ, comprising administering a sufficient amount of a radiolabelled compound of formula (I) as defined by claim 1, and detecting the emissions from the radioactive compound.

* * * * *